United States Patent [19]

DiPalma et al.

[11] Patent Number: 5,609,588
[45] Date of Patent: Mar. 11, 1997

[54] ARTICLE HAVING A NON-ABSORBENT RESILIENT LAYER

[75] Inventors: Joseph DiPalma; David R. King, both of Neenah; Thomas H. Gilman, Appleton; Laurie Couture-Dorschner, Hortonville; Timothy S. Stilp, Appleton; Valerie V. Finch, Neenah, all of Wis.

[73] Assignee: Kimberly-Clark Corporation, Neenah, Wis.

[21] Appl. No.: 255,840

[22] Filed: Jun. 8, 1994

Related U.S. Application Data

[63] Continuation of Ser. No. 891,361, May 29, 1992, abandoned.

[51] Int. Cl.[6] ................ A61F 13/15; B32B 7/12
[52] U.S. Cl. .......... 604/369; 604/378; 604/387; 428/337; 428/332
[58] Field of Search .................. 604/358, 365, 604/366, 368–370, 372–387, 389–390; 2/78 C, 401; 428/332, 337

[56] References Cited

U.S. PATENT DOCUMENTS

| Re. 32,649 | 4/1988 | Brandt et al. | 604/368 |
|---|---|---|---|
| 2,295,439 | 9/1942 | Voigtman | 128/284 |
| 2,564,689 | 8/1951 | Harwood et al. | 128/290 |
| 2,587,459 | 2/1952 | Fuentes | 128/290 |
| 2,731,014 | 1/1956 | Hollingsworth | 128/290 |
| 2,900,980 | 8/1959 | Harwood | 128/290 |
| 3,088,462 | 5/1963 | Muto | 128/290 |
| 3,461,872 | 8/1969 | McConnell et al. | 128/287 |

(List continued on next page.)

FOREIGN PATENT DOCUMENTS

| 0165807A1 | 12/1985 | European Pat. Off. . |
|---|---|---|
| 0248584A2 | 12/1987 | European Pat. Off. . |
| 0293208A1 | 11/1988 | European Pat. Off. . |
| 0298348 | 1/1989 | European Pat. Off. . |
| 0339461A1 | 11/1989 | European Pat. Off. . |
| 0359501A2 | 3/1990 | European Pat. Off. . |
| 0148855 | 6/1981 | German Dem. Rep. ........... 2/401 |
| 40-36391 | 12/1965 | Japan . |
| 46-12554 | 5/1971 | Japan . |
| 2168612 | 6/1986 | United Kingdom . |
| WO91/00719 | 1/1991 | WIPO . |

OTHER PUBLICATIONS

Rubber Technology, 2nd ed., Maurice Morton, ed., 1973 pp. 518–520, 568.
Handbook of Plastics and Elastomers, Harper ed., 1975, pp. 1-3—1-4, 1-106—107 1-111—112, 3-114, 3-69, 3-70, 3-72, 3-76, 7-30, 7-35, 7-52.
Websters New International Dictionary, Unabridged, "elastic", p. 824.
Grant & Hackh's Chemical dictionary, "resilience", p. 503, elastomer, p. 201.
American Society for Testing Material (ASTM), Publications D 3575–84; D 3574–86; D 1054–87; and D 4032–82.
Encyclopedia of Polymer Science and Engineering, vol. 3, pp. 6 and 7, John Wiley and Sons, New York, New York 1985.
Technical Association of the Pulp and Paper Industry (TAPPI), Method T 543 pm—84.

*Primary Examiner*—John G. Weiss
*Assistant Examiner*—K. M. Reichle
*Attorney, Agent, or Firm*—Mark L. Davis

[57] ABSTRACT

An absorbent article, such as a sanitary napkin, has an absorbent and a substantially non-absorbent resilient layer adjacent to the absorbent. The absorbent is sufficiently stiff to resist twisting of the absorbent article during use. The resilient layer is sufficiently resilient to resist bunching during use. As a result, the absorbent article resists both twisting and bunching. The absorbent article has zones which vary in caliper, stiffness and absorbency. A central absorbent zone is thickest in caliper, more absorbent than the other zones and is stiffer than the other zones. An adjacent zone is less thick in caliper, less absorbent and less stiff. A peripheral zone, located near the outer side edges, is least thick in caliper, least absorbent and least stiff.

24 Claims, 9 Drawing Sheets

U.S. PATENT DOCUMENTS

| | | | |
|---|---|---|---|
| 3,570,493 | 3/1971 | Olsson | 128/290 |
| 3,779,246 | 12/1973 | Mesek et al. | 128/287 |
| 3,805,790 | 4/1974 | Kaczmarzyk et al. | 128/290 R |
| 3,828,786 | 8/1974 | Cervantes | 128/290 R |
| 3,881,490 | 5/1975 | Whitehead et al. | 128/287 |
| 3,888,255 | 6/1975 | Shah et al. | 128/290 R |
| 3,916,900 | 11/1975 | Breyer et al. | 128/287 |
| 3,981,306 | 9/1976 | Krusko | 128/287 |
| 3,993,074 | 11/1976 | Murray et al. | 128/286 |
| 4,057,061 | 11/1977 | Ishikawa et al. | 128/284 |
| 4,079,739 | 3/1978 | Whitehead | 128/290 R |
| 4,195,634 | 4/1980 | DiSalvo et al. | 128/290 R |
| 4,217,901 | 8/1980 | Bradstreet et al. | 128/290 R |
| 4,306,559 | 12/1981 | Nishizawa et al. | 128/287 |
| 4,315,507 | 2/1982 | Whitehead et al. | 128/287 |
| 4,324,246 | 4/1982 | Mullane et al. | 128/287 |
| 4,340,058 | 7/1982 | Pierce et al. | 128/287 |
| 4,341,216 | 7/1982 | Obenour | 128/287 |
| 4,347,092 | 8/1982 | Hlaban et al. | 156/227 |
| 4,376,440 | 3/1983 | Whitehead et al. | 604/387 |
| 4,389,211 | 6/1983 | Lenaghan | 604/383 |
| 4,397,644 | 8/1983 | Matthews et al. | 604/378 |
| 4,402,689 | 9/1983 | Baum | 604/387 |
| 4,423,101 | 12/1983 | Willstead | 428/76 |
| 4,467,012 | 8/1984 | Pedersen et al. | 428/248 |
| 4,475,913 | 10/1984 | Hlaban | 604/387 |
| 4,490,147 | 12/1984 | Pierce et al. | 604/378 |
| 4,534,769 | 8/1985 | De Jonckhere et al. | 604/369 |
| 4,536,433 | 8/1985 | Sagi et al. | 428/195 |
| 4,554,191 | 11/1985 | Korpman | 428/35 |
| 4,578,066 | 3/1986 | O'Connor | 604/366 |
| 4,610,678 | 9/1986 | Weisman et al. | 604/368 |
| 4,624,666 | 11/1986 | DeRossett et al. | 604/366 |
| 4,657,538 | 4/1987 | Becker et al. | 604/381 |
| 4,675,013 | 6/1987 | Ruffo | 604/366 |
| 4,681,578 | 7/1987 | Anderson et al. | 604/385 R |
| 4,681,793 | 7/1987 | Linman et al. | 428/138 |
| 4,704,107 | 11/1987 | Coates | 604/357 |
| 4,710,186 | 12/1987 | DeRossett et al. | 604/383 |
| 4,713,068 | 12/1987 | Wang et al. | 604/366 |
| 4,713,069 | 12/1987 | Wang et al. | 604/378 |
| 4,725,473 | 2/1988 | Van Gompel et al. | 428/156 |
| 4,737,404 | 4/1988 | Jackson | 428/284 |
| 4,738,676 | 4/1988 | Osborn, III | 604/385 R |
| 4,741,941 | 5/1988 | Englebert et al. | 428/71 |
| 4,753,644 | 6/1988 | Cottenden et al. | 604/378 |
| 4,758,239 | 7/1988 | Yeo et al. | 604/366 |
| 4,773,904 | 9/1988 | Nakanishi et al. | 604/372 |
| 4,798,603 | 1/1989 | Meyer et al. | 604/378 |
| 4,801,494 | 1/1989 | Datta et al. | 428/283 |
| 4,818,600 | 4/1989 | Braun et al. | 428/290 |
| 4,828,556 | 5/1989 | Braun et al. | 604/365 |
| 4,834,739 | 5/1989 | Linker, III et al. | 604/385.1 |
| 4,850,991 | 7/1989 | Nakanishi et al. | 604/387 |
| 4,891,258 | 1/1990 | Fahrenkrug | 428/138 |
| 4,908,026 | 3/1990 | Sukiennik et al. | 604/378 |
| 4,950,264 | 8/1990 | Osborn, III | 604/385.1 |
| 4,963,139 | 10/1990 | Dabroski | 604/378 |
| 4,969,970 | 11/1990 | Suzuki et al. | 156/495 |
| 5,009,653 | 4/1991 | Osborn, III | 604/385.1 |
| 5,011,480 | 4/1991 | Gossens et al. | 604/385.1 |
| 5,013,309 | 5/1991 | Baigas, Jr. et al. | 604/368 |
| 5,019,422 | 5/1991 | Rose et al. | 427/245 |
| 5,091,240 | 2/1992 | Kajander et al. | 428/198 |
| 5,248,309 | 9/1993 | Serbiak et al. | 604/368 |

ARTICLE HAVING A NON-ABSORBENT RESILIENT LAYER

This application is a continuation of U.S. application Ser. No. 07/891,361, filed May 29, 1992, now abandoned.

FIELD OF THE INVENTION

This invention relates to an absorbent article, such as a sanitary napkin. More specifically, this invention relates to an absorbent article which has a substantially non-absorbent, substantially resilient layer to resist bunching during use.

BACKGROUND OF THE INVENTION

The term "absorbent article" relates to products such as sanitary napkins, incontinent products, diapers, panty liners, training pants and the like. Sanitary napkins, also referred to as catamenial or feminine pads, are designed to be worn by a female to absorb medium to heavy flow of body fluids such as menses, blood, urine, and other excrements discharged by the body during a menstrual period. Sanitary napkins are external devices which are designed to be aligned approximate to the pudendum region of the human body and are generally held in position by being adhesively or mechanically attached to an undergarment. Such products differ from tampons which are classified as internal devices and are designed to be physically inserted into the vaginal cavity. Sanitary napkins also differ from pantiliners and panty shields in several noticeable ways. Most sanitary napkins are generally larger in size, have a more defined three-dimensional configuration, are thicker in caliper and are bulkier in appearance than pantiliners or panty shields. Functionally, sanitary napkins are different in that they are constructed to absorb a greater quantity of body fluid and are designed so that they can be worn for a longer period of time, for example, overnight if needed.

Since sanitary napkins are normally used during the major discharge portion of a menstrual period, they are constructed to handle medium to heavy flows and commonly have a total absorbent capacity in the range of about 20 to 50 grams of fluid. Pantiliners and panty shields, on the other hand, are designed to absorb relatively small amounts of body fluids and are marketed to be used at the beginning and end of a menstrual period when flow is light or spotty. Commercially available pantiliners and panty shields are constructed to have a total absorbent capacity in the range of about 1 to 15 grams of fluid.

Today's sociological changes have led to more women becoming active in sports and other types of physical activity. These changes have been accompanied by a change in attire and have led to more women wearing tight, body-fitting clothing. Most current sanitary napkins, having a caliper of 6.4 mm. or greater, can present an unsightly bulge adjacent the pudendum when worn inside tight-fitting shorts or pants. The overall size and configuration of the napkin can also restrict leg movement or cause discomfort when a woman participates in physical or sporting events. In view of this, there is a real need to provide an improved thin sanitary napkin which is less than about 5 millimeters in caliper and resists bunching and twisting when worn.

In providing a thin sanitary napkin less than about 5 millimeters in caliper, it was found that such products had a tendency to bunch and twist when worn. The squeezing of the napkin between the thighs and the resulting deformation as a woman moves about, causes the upper surface of the napkin to acquire a curved or convex shape. The twisting is sometimes referred to as "roping" because of twisting along a longitudinal axis that imparts a cylindrical profile to the sanitary napkin. The roping effect is detrimental because the napkin is unable to absorb body fluid that contacts its upper surface. The fluid discharged from the vagina has a tendency to run off the roped napkin before it can be absorbed by the primary absorbent means in the sanitary napkin and, therefore, the fluid leaks on an adjacent undergarment. This run-off becomes significant during periods of heavy flow. Such bunching and twisting is more of a problem in thin sanitary napkins than in thicker napkins.

Other people have recognized the need for a thin sanitary napkin. See, for example: U.S. Pat. Nos. 4,217,901 to Bradstreet et al.; 4,950,264 and 5,009,653 to Osborn; and U.S. Pat. No. 5,248,309 to Serbiak et al. assigned to the same owner as this Patent Application.

SUMMARY OF THE INVENTION

This invention relates to an absorbent article such as a sanitary napkin which has a central longitudinal axis. The absorbent article has an absorbent means and a substantially nonabsorbent, substantially resilient layer or member adjacent to the absorbent means. The absorbent means has a central longitudinal axis substantially aligned along the central longitudinal axis of the absorbent article. The absorbent article may also have a liquid pervious cover sheet. In addition, the absorbent article may have a liquid impervious backing sheet or baffle. The absorbent means is sufficiently stiff to resist twisting of the absorbent article during use. The resilient layer has a width within the range of from 60 percent to 100 percent of the total width of the absorbent article and is sufficiently resilient to resist bunching of the absorbent article during use. The absorbent means may be located between the cover sheet and the substantially resilient layer. The resilient layer has a Circular Bend Flex in the range of from about 9 to about 42 grams. The absorbent means has a Gurley stiffness in the range of from about 782 milligrams to about 2526 milligrams. Desirably, the absorbent article has a total width that spans the width of the labia majora of the user.

For absorbent articles such as sanitary napkins, the sanitary napkin may also have a transfer layer, one or more tissue layers, a garment adhesive on the garment-facing side of the sanitary napkin and a peel strip over the garment adhesive and adapted to be removed before use to expose the garment adhesive. In one embodiment, the sanitary napkin has a liquid pervious cover sheet, a substantially liquid impervious backing sheet, an absorbent means, and a substantially nonabsorbent, substantially resilient layer disposed between the absorbent means and the backing sheet. The backing sheet is at least partially peripherally joined to the cover sheet. The sanitary napkin has a total width transverse to the longitudinal axis which is defined by the distance from one outer side edge of the sanitary napkin to the opposite outer side edge of the sanitary napkin of the body-facing side of the napkin.

The absorbent means has a longitudinal central axis substantially aligned along the longitudinal central axis of the sanitary napkin. The absorbent means is sufficiently stiff to resist twisting of the sanitary napkin during use. The resilient layer is disposed between the absorbent means and the backing sheet. The resilient layer has a width within the range of from 60 percent to 100 percent of the total width of the sanitary napkin and is sufficiently resilient to resist bunching of the sanitary napkin during use. The absorbent means may have a width of less than 2.5 inches (63.5 millimeters). Alternately, it may have a width of less than 60 percent of the total width of the body-facing side of the sanitary napkin. The sanitary napkin may have a caliper or thickness of less than about 5 millimeters (mm.).

One object of this invention is to provide an absorbent article which resists twisting and bunching during use. Another object of this invention is to provide a thin sanitary napkin which has a central longitudinal absorbent zone which is more absorbent and stiffer than adjacent zones, in combination with a resilient layer that is substantially nonabsorbent. Still another object of the present invention is to provide an absorbent article that has zones that vary in caliper, stiffness and absorbency. A central absorbent zone is thickest in caliper, is more absorbent than any of the other zones and is the stiffest of any of the other zones. An adjacent zone, which is adjacent to the absorbent zone is less thick in caliper, less absorbent and less stiff. A peripheral zone, located near the outer side edges, is still less thick in caliper, less absorbent and less stiff.

The invention further includes a method for achieving improved performance in a sanitary napkin, including the steps of: providing a substantially resilient layer substantially aligned along the central, longitudinal axis of the napkin to resist bunching, providing a stiffening means substantially aligned along the central, longitudinal axis of said napkin and adapted to resist twisting of said napkin, arranging the substantially resilient layer so that its width extends across at least 60% of the total width of the body-facing surface of the napkin, and selecting for the stiffening means a material having comparatively high absorbent capacity and adapted to absorb fluid adjacent to the central, longitudinal axis of the napkin and thereby reduce flow of fluid toward the outer side edges of the napkin to reduce leakage of fluid at the outer side edges of the napkin. The method may also include the step of selecting for the substantially resilient layer a material that is substantially non-absorbent to further reduce leakage at the outer side edges of the napkin.

We have found that the combination of elements in absorbent articles of the invention described herein, such as sanitary napkins, provides products having unexpectedly good results and achieves a good balance between comfort to the user when worn, high absorbency and other good performance characteristics and reasonable cost. The products have a softness and thinness around the edges that enhance comfort. The products also resist twisting, bunching and leakage.

DETAILED DESCRIPTION

The absorbent article may be a sanitary napkin which is designed to be worn by a female to absorb body fluids such as menses, blood, urine, and other excrements, such as those discharged during a menstrual period.

First Embodiment

Figure 1:
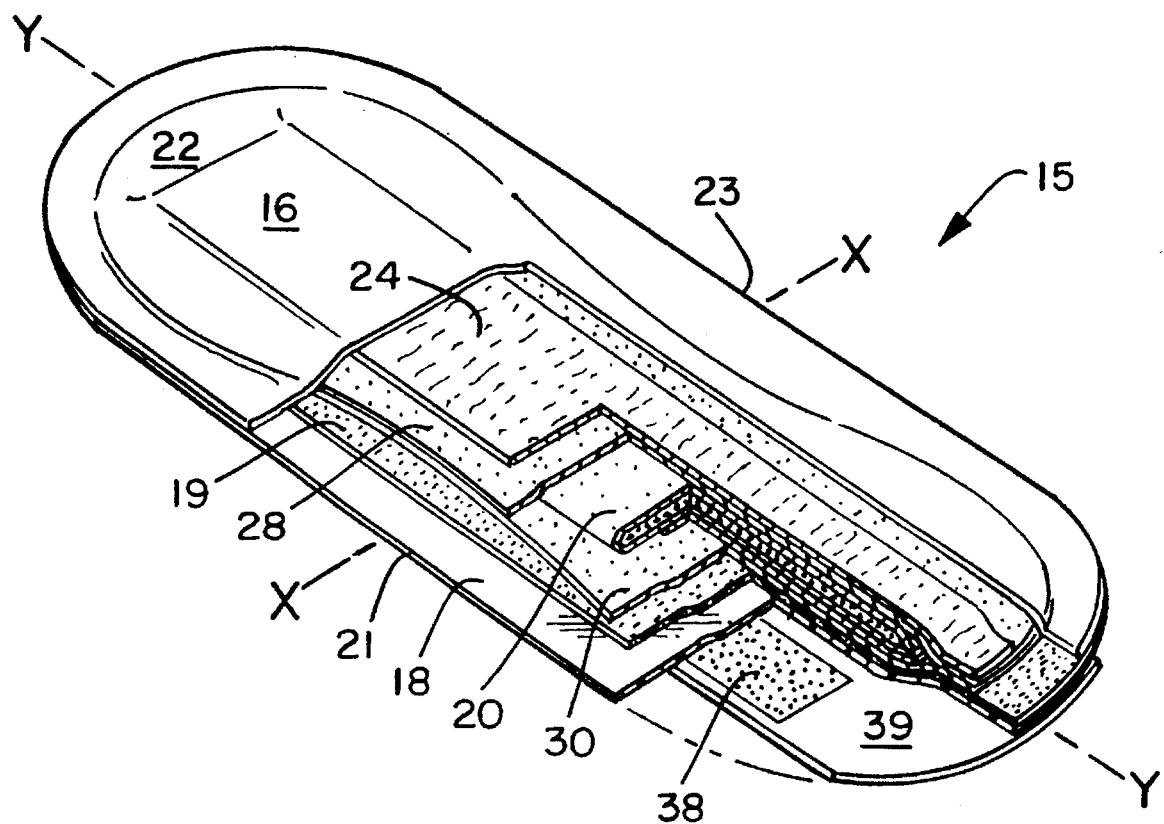
FIG. 1 is a perspective view of a first embodiment of the invention, with a portion broken away to show internal components.
Figure 2:
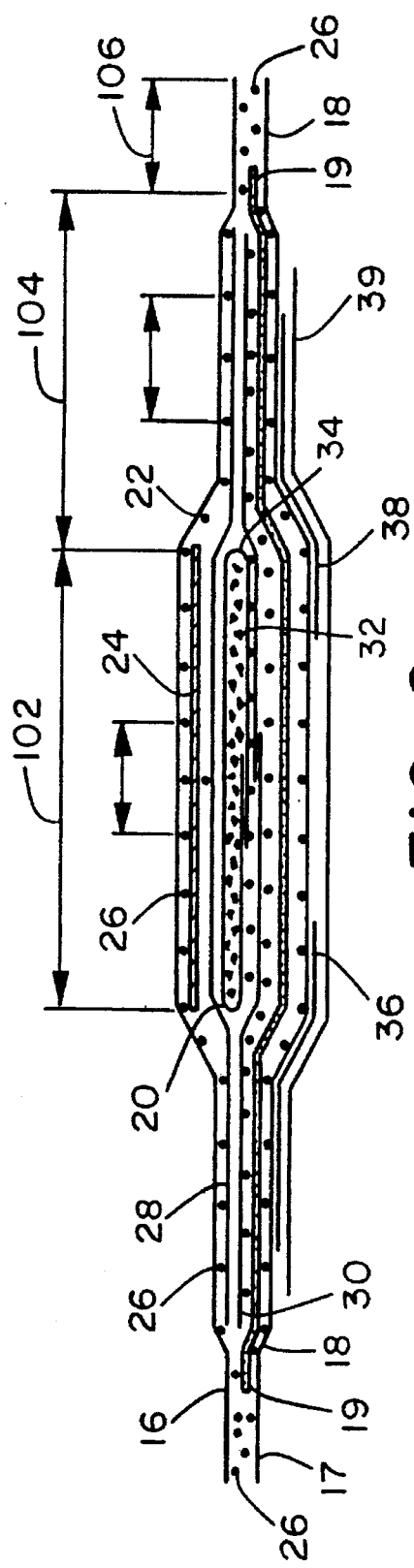
FIG. 2 is a schematic illustration of a cross-sectional view of FIG. 1 along the lines X—X.
Figure 3:
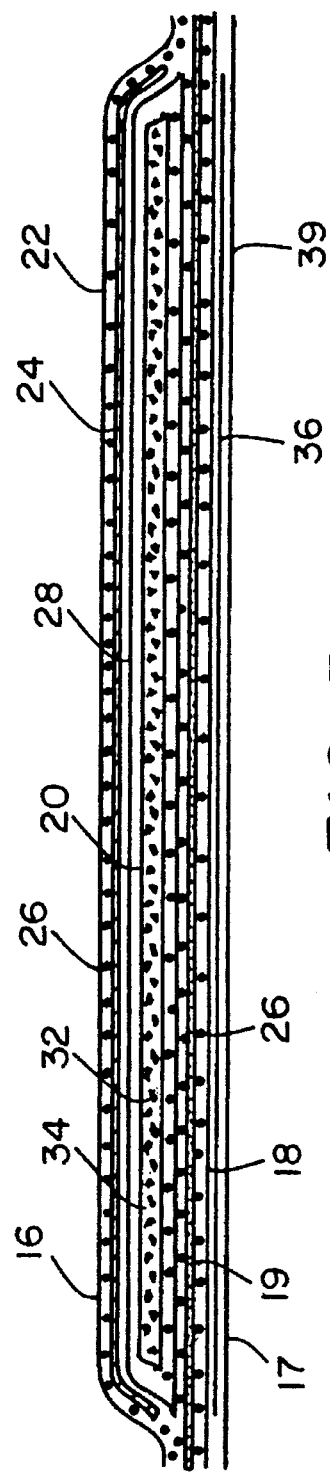
FIG. 3 is a schematic illustration of a cross-sectional view of FIG. 1 along the lines Y—Y.

Referring to FIGS. 1, 2, and 3, a first embodiment of the sanitary napkin 15 is about 150 millimeter (mm.) to 320 mm. long, about 60 mm. to 120 mm. wide and has rounded ends. The sanitary napkin 15 is relatively thin and has a caliper or thickness of less than about 5 millimeters, more desirably less than about 4 millimeters, and most desirably less than about 3 millimeters. The sanitary napkin 15 has a body-facing side 16, a garment-facing side 17, a substantially liquid-impermeable backing sheet or baffle 18, a substantially nonabsorbent, resilient layer 19 and an absorbent means 20.

The resilient layer 19 is made of one or more layers of a flexible, closed cell, polyethylene foam material. An example of a foam used in this embodiment may be purchased from Sealed Air Corporation, 7110 Sante Fe Drive, Hodgkins, Ill. 60525 U.S.A. The grade specification is:"CELL-AIRE" Foam, CA-30, thickness of ⅟₃₂ inch, density of 1.2 pounds per cubic foot, width of 60 inches, on rolls having a linear length of 2000 feet. Ametek Microfoam Division, Brandwine Four Building, Routes 1 and 202, Chadds Ford, Pa. 19317 U.S.A., produces a light weight polypropylene foam that is also suitable for this embodiment. The foam is called "MICROFOAM".

The resilient layer 19 is located adjacent to and on the body-facing side of the baffle 18. The absorbent means 20 is located on the opposite side of the resilient layer 19 from the baffle 18. The absorbent means 20 is substantially aligned along the central longitudinal axis Y—Y of the sanitary napkin 15. The resilient layer 19 has a width greater than the width of the absorbent means 20. The resilient layer 19 has a length equal to, and desirably greater than, the absorbent means 20. The resilient layer 19 has a length of at least 60% of the length of the napkin 15.

The baffle 18 is designed to face the inner surface, generally the crotch portion, of an undergarment (not shown). The baffle 18 blocks the passage of body fluids and other liquids. The baffle 18 can be made from micro-embossed polymeric films such as polyethylene or polypropylene, or it can be made from bicomponent films. A preferred material is polyethylene film.

The absorbent means 20 has an overall length that extends at least about 50%, and desirably at least about 75%, of the length of the napkin 15. The absorbent means 20 has a width of less than about 2.5 inches (63.5 mm.), desirably less than about 2 inches (50.8 mm.), more desirably between about 0.5 and 2.0 inches (12.7 mm. and 50.8 mm.), and most desirably about 1.25 inches (31.8 mm.) or 1.50 inches (38.1 mm.) when measured across the central transverse axis Y—Y of the napkin 15. Desirably, the absorbent means 20 has a width which is less than about 60% of the total width of the body-facing side of the sanitary napkin 15 when measured across the narrowest portion of the napkin 15. The total width of the sanitary napkin 15 is measured along an axis, such as axis X—X in FIG. 1, transverse to the longitudinal axis Y—Y of sanitary napkin 15. The total width of the sanitary napkin 15 is the distance from one outer side edge 21 to the opposite outer side edge 23 of the body-facing side of the napkin. Desirably, the width of the napkin spans the width of the labia majora of the user. The absorbent means 20 has sufficient stiffness to enable the sanitary napkin 15 to resist twisting and "roping", as a result of its stiffness. The absorbent means 20 does not extend the full width of the sanitary napkin 15 in order to enhance comfort to the wearer. Arranging the absorbent means 20 substantially in the center, that is, in substantial alignment with the central longitudinal axis Y—Y of the sanitary napkin 15, provides the advantage of placing the absorbent means 20 close to the source of fluid.

The resilient layer 19 has sufficient resilience to resist bunching of the sanitary napkin 15. The combination of the resilient layer 19 and the absorbent means 20 resists both twisting and bunching. The resilient layer 19 is not as stiff as the absorbent means 20 and, for that reason, is arranged to be wider than the absorbent means 20. Desirably the width of the resilient layer 19 is in the range of 60% to 100% of the total width of the sanitary napkin 15.

The absorbent means 20 constitutes the significant absorbing portion of the napkin 15 and has the capability of absorbing at least about 80%, desirably about 90%, and most desirably about 95% of the body fluid deposited on the napkin 15. In terms of amount of body fluid, the absorbent means 20 can absorb at least 10 grams, desirably about 20 grams, and most desirably, about 30 grams or more of body fluid. Thus, the absorbent means 20 is both the primary absorbent and a stiffening means.

On the body-facing side 16 of the sanitary napkin 15, there is a cover layer 22 on the outside of the sanitary napkin 15. Inside the cover layer 22 and adjacent to it, there is a transfer layer 24. There is construction adhesive 26 between the transfer layer 24 and the cover layer 22. In FIGS. 2 and 3, the construction adhesive 26 is represented by a series of dots in various locations and between various layers or components in the sanitary napkin 15.

The cover layer 22 is liquid-permeable and is designed to contact the body of the wearer. It can be constructed of a woven or non-woven, natural or synthetic material which is easily penetrated by body fluid. Suitable materials include bonded carded webs of polyester, polypropylene, nylon, or other heat-bondable fibers. Other polyolefins such as copolymers of polypropylene and polyethylene, linear low-density polyethylene, finely-perforated film webs and net material also work well. A preferred material is a spunbonded polypropylene, non-apertured web which contains about 1 to 6% titanium dioxide pigment to give it a clean white appearance. A white uniform spunbonded material is desirable because the color exhibits good masking properties to hide menses which has passed through it and the material has sufficient strength to resist being torn. U.S. Pat. Nos. 4,801,494 issued to Datta et al. and 4,908,026 issued to Sukiennik et al. describe various cover materials which can be used with the sanitary napkin 15. The description in the two patents is incorporated herein by reference and made a part hereof.

The liquid-permeable cover layer 22 can also contain a plurality of apertures formed therein and the apertures can be arranged along the longitudinal center line Y—Y, if desired. The apertures will increase the rate at which body fluids can penetrate down into the absorbent means 20. The cover layer 22 may also be treated with a surfactant to make it more hydrophilic. The surfactant may include topical additions or internally applied materials such as polysiloxanes.

The transfer layer 24 is made of an absorbent nonwoven polypropylene meltblown web which facilitates movement of body fluid downward and outward from the cover 22 to distant areas of the central absorbent means 20. In the alternative, the transfer layer 24 may be made of an absorbent nonwoven polypropylene spunbond web or other material having similar properties. Desirably, the transfer layer 24 is aligned along the central longitudinal axis Y—Y of the sanitary napkin 15 and is sized and configured to correspond to the shape and dimensions of the central absorbent means 20. Desirably also, the transfer layer 24 is slightly longer than the absorbent means 20. A description of a transfer layer is taught in U.S. Pat. No. 4,798,603 issued to Meyer et al. and assigned to the present assignee. This patent is incorporated by reference and made a part hereof.

The transfer layer 24 has a width approximately equal to the absorbent means 20. The cover layer 22 has a width approximately equal to the width of the sanitary napkin 15 and the cover layer 22 extends out to the periphery of the sanitary napkin 15. A first tissue layer 28 is located between the transfer layer 24 and the absorbent means 20. The first tissue layer 28 has a width greater than the width of the transfer layer 24 and greater than the width of the absorbent means 20. During use, menses or other body fluid first contacts the cover layer 22, then reaches the transfer layer 24, then reaches the first tissue layer 28 and then reaches the absorbent means 20.

The body-facing side of the transfer layer 24 has adhesive 26 over substantially the entire surface of the body-facing side of the transfer layer 24. The garment-facing side of the transfer layer 24 does not have adhesive over the entire surface of the garment-facing side. Instead, the garment-facing side of the transfer layer 24 has a single line of adhesive 26 in the middle of the transfer layer 24, between the transfer layer 24 and the first tissue layer 28.

The cover layer 22 has a body-facing side and a garment-facing side. The garment-facing side of the cover layer 22 has adhesive over its entire surface. As a result, there is adhesive 26 between the transfer layer 24 and the cover layer 22. In addition, there is adhesive 26 between the cover layer 22 and the first tissue layer 28. There is no adhesive between the first tissue layer 28 and the absorbent means 20.

The absorbent means 20 has a body-facing side and a garment-facing side. On the garment-facing side of the absorbent means 20, and between it and the resilient layer 19, there is a second tissue layer 30. The second tissue layer 30 has a width approximately equal to the width of the first tissue layer 28. Both tissue layers have a width which is greater than the width of the absorbent means 20 and, desirably, greater than two times the width of the absorbent means 20. There is adhesive 26 between the garment-facing side of the absorbent means 20 and the second tissue layer 30.

The second tissue layer 30 has a body-facing side and a garment-facing side. The garment-facing side of the second tissue layer 30 is adjacent to the resilient layer 19. Between the second tissue layer 30 and the resilient layer 19 there is adhesive 26 which extends over a portion of the garment-facing side of the second tissue layer 30 and a portion of the body-facing side of the resilient layer 19. The area over which there is adhesive 26 between the second tissue layer 30 and the resilient layer 19 is an area slightly less than the area of the garment-facing side of the absorbent means 20.

There is adhesive between the body-facing side of the second tissue layer 30 and the absorbent means 20. At the ends of the sanitary napkin 15, there is adhesive between the first tissue layer 28 and the second tissue layer 30. The resilient layer 19 has a body-facing side and a garment-facing side. The baffle 18 is located on the garment-facing side of the resilient layer 19. There is adhesive 26 between the resilient layer 19 and the baffle 18.

If the resilient layer 19 is too thick or too stiff, or both, such thickness or stiffness may interfere with comfort to the wearer. It has been found that a thin resilient layer 19 is effective if it is adhered or bonded to the baffle 18. Such a resilient layer 19 bonded to the baffle 18 achieves the desired stiffness and thus the desired resistance to bunching and yet allows a thinner resilient layer 19 to be used than if the resilient layer 19 were not bonded to the baffle 18. The thinner resilient layer 19 bonded to the baffle 18 provides more comfort to the user than a thicker resilient layer 19. Bonding the film baffle 18 to the resilient layer 19 of foam also facilitates use of a garment adhesive. It is easier to use a garment adhesive on a film baffle 18 than placing the garment adhesive on a resilient layer 19 made of foam.

Thus, bonding the foam layer to the film baffle 18 enhances comfort, achieves a thinner product and is more economical than a thicker layer of foam. It is desirable to use a layer of foam that is ⅛ inch (3.175 mm.) thick or less. More desirably, one should use a layer of foam that is 1/16 inch (1.587 mm.) in thickness or less. Even more desirably, one should use a layer of film that is 1/32 inch (0.793 mm.) in thickness.

Referring to FIG. 1, the first tissue layer 28 and the second tissue layer 30 have an hourglass shape. As a result, the width of the first tissue layer 28 and the second tissue layer 30 is slightly greater at each end of the first tissue layer 28 and the second tissue layer 30. As a result, the width of the first tissue layer 28 and the second tissue layer 30, measured along the axis X—X, is less than the width at the outer ends of the first tissue layer 28 and the second tissue layer 30.

The cover layer 22 and the baffle 18 extend to the outer periphery of the sanitary napkin 15. At their outer periphery all around the sanitary napkin 15, the cover layer 22 and the baffle 18 are joined together by adhesive. At the sides of the napkin 15, the resilient layer 19 extends close to the outer periphery of the sanitary napkin 15, but within the periphery of the sanitary napkin 15. As a result, the width of the resilient layer 19 is slightly less than the width of the cover layer 22 and the baffle 18. At the ends of the napkin 15, the resilient layer 19 desirably extends to the outer edge of the napkin 15. As a result, at the ends of the napkin 15, the length of the resilient layer 19 is equal to the length of the cover layer 22 and the baffle 18. The first tissue layer 28 and the second tissue layer 30 have a size which is slightly less than the size of the resilient layer 19, both in length and in width.

Referring to FIG. 2, the absorbent means 20 is constructed as a laminate comprised of a hydrocolloidal material 32 positioned within a carrier layer 34 that is a folded hydrophilic material such as an airlaid tissue. The hydrocolloidal material 32, commonly referred to as a superabsorbent, can be a hydrogel-forming polymer composition which is water-insoluble, slightly cross-linked, and partially neutralized. It can be prepared from an unsaturated polymerizable, acid group-containing monomers and cross-linked agents. Such superabsorbents are taught in U.S. Pat. Nos. 4,798,603 issued to Meyers et al., Re. 32,649 issued to Brandt et al. and 4,467,012 issued to Petersen et al., as well as in published European Patent Application 0 339 461 to Kellenberger. These U.S. Patents and the European Patent Application are incorporated herein by reference and made a part hereof.

Superabsorbents are very good at retaining body fluids. They have the ability to absorb a great amount of fluid in relation to their own weight. Typical superabsorbents used in sanitary napkins can absorb anywhere from 5 to 60 times their weight in blood. However, the absorption mechanism is not a rapid absorption and is usually slower than the rate of fluid absorption by the cellulose fluff material. The placement of the superabsorbent material in the center or lower portion of the napkin provides additional time for the superabsorbent to absorb the fluid from the transfer layer 24.

It has been found that superabsorbents having a high mechanical stability in the swollen state, an ability to rapidly absorb fluid, and ones having a strong liquid binding capacity perform well in catamenial devices. Hydroxyfunctional polymers have been found to be good superabsorbents for this application. A hydrogel-forming polymer, specifically a partially neutralized cross-linked copolymer of polyacrylic acid and polyvinyl alcohol is desirable. Such superabsorbents can be obtained from Dow Chemical, Hoechst-Celanese, and Stockhausen, Inc., among others. The superabsorbent is a partially neutralized salt of cross-linked copolymer of polyacrylic acid and polyvinyl alcohol having an absorbency under load value about 25.

The superabsorbent should have a high absorbency under load, that is, it should have the ability to expand or swell under a restraining pressure, typically about 0.3 pound per square inch (psi). The absorbency under load value is a function of gel strength, osmotic pressure within the gel and the composition of the polymer itself. The absorbency under load value also pertains to the ability of the gel to swell against other superabsorbent particles as well as against adjacent fibers when under pressure. For purposes of this invention, a superabsorbent having a high absorbency under load is defined as having a value of 20 or higher. A desirable absorbency under load value is 25 or higher. The test for determining an absorbency under load value is taught on page 7, lines 14–52 of published European Patent Application 0 339 461 (Kellenberger) and assigned to the present assignee. In the alternative, the absorbent means 20 may be a composite comprised of a hydrophilic material and a hydrocolloidal material. The hydrophilic material can be various natural or synthetic fibers, including cellulose fibers, surfactant-treated meltblown fibers, wood pulp fibers, regenerated cellulose or cotton fibers, or a blend of pulp and other fibers.

The baffle 18 has a body-facing side and a garment-facing side. The sanitary napkin 15 also contains two longitudinally-extending strips of garment adhesive 36 and 38 which are attached to the exterior surface, that is, the garment-facing side, of the baffle 18. The garment adhesive is commercially available from National Starch and Chemical Company, located at 10 Finderne Ave., Bridgewater, N.J. 08807 U.S.A. The strips of garment adhesive 36 and 38 are used to secure the sanitary napkin 15 to the inside of the crotch portion of an undergarment so that it can be properly aligned with the vaginal opening. A peel strip 39 is releasably attached to the garment adhesive strips 36 and 38 and prevents the adhesive from becoming contaminated prior to attachment to the undergarment. The peel strip 39 can be a white Kraft paper coated on one side so that it can be released from a hot melt adhesive. The peel strip 39 is designed to be removed by the ultimate consumer just prior to placement of the sanitary napkin 15 in the undergarment.

Second Embodiment

Figure 4:
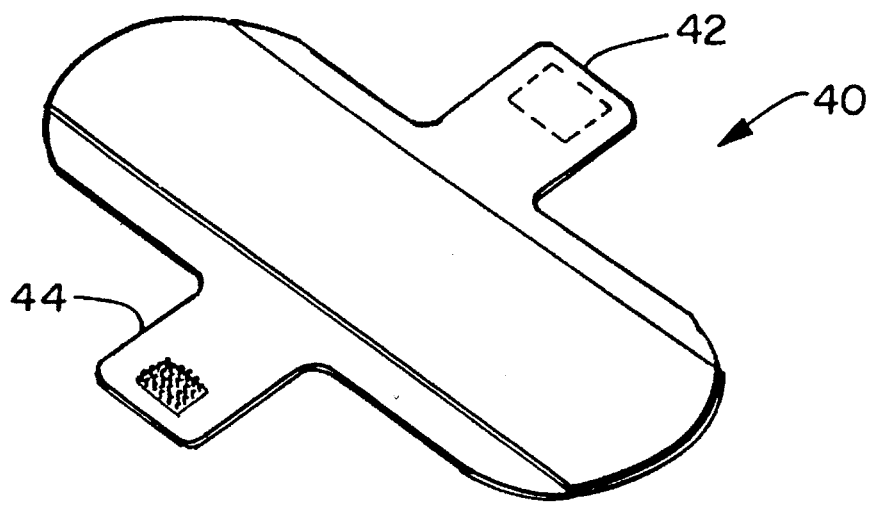
FIG. 4 is a perspective view of a second embodiment of the invention.

Referring to FIG. 4, a second embodiment of the invention is a sanitary napkin 40 that has two tabs 42 and 44, one tab arranged on each side of a sanitary napkin 40. In other respects, the sanitary napkin 40 is similar to the sanitary napkin 15 illustrated in FIGS. 1, 2 and 3. The tabs 42 and 44 are intended to be folded around the undergarment of the user and to increase the attachment of the sanitary napkin 40 to the garment.

Third Embodiment

Figure 5:
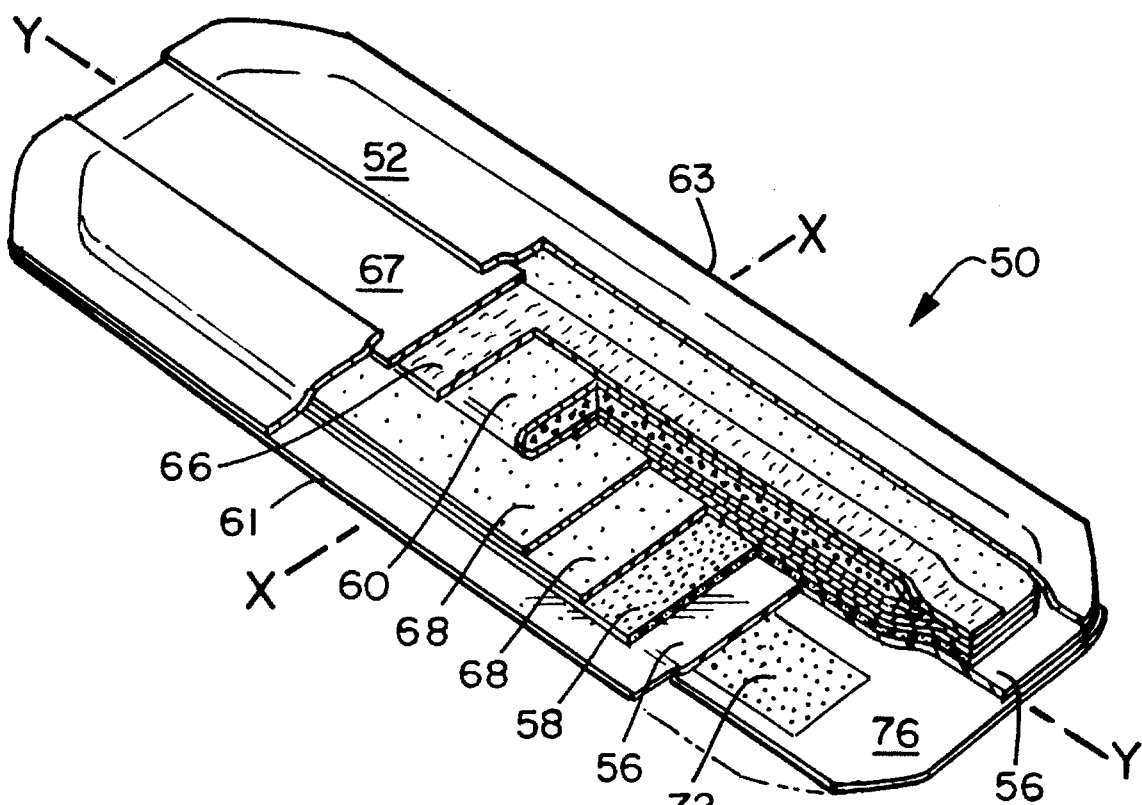
FIG. 5 is a perspective view of a third embodiment of the invention with a portion broken away to show internal components.
Figure 6:
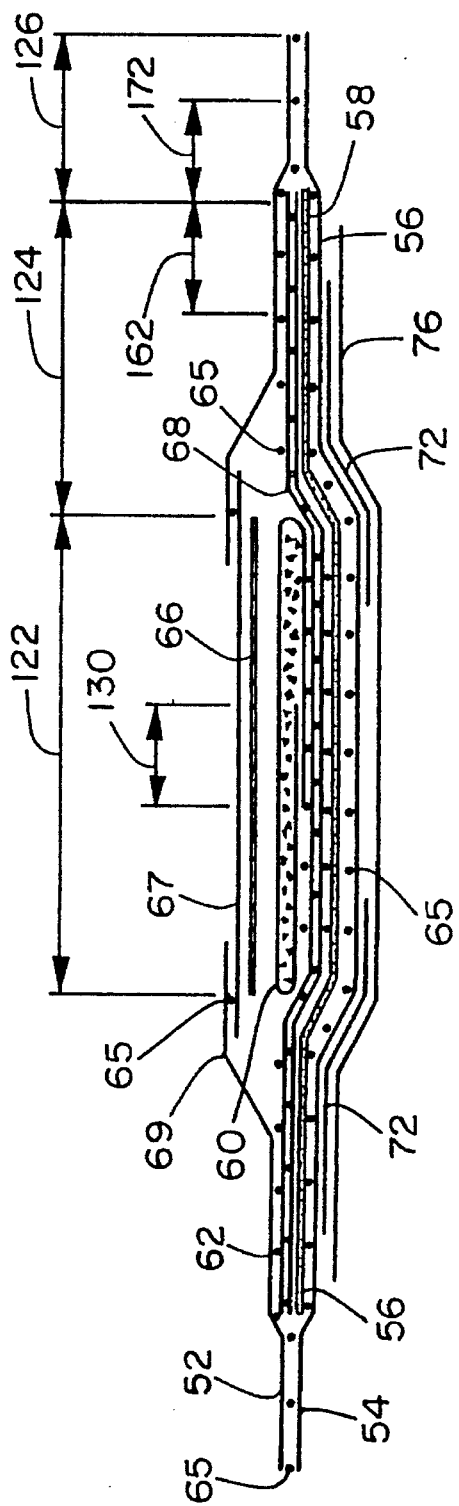
FIG. 6 is a schematic illustration of a cross-sectional view of FIG. 5 along the lines X—X.
Figure 7:
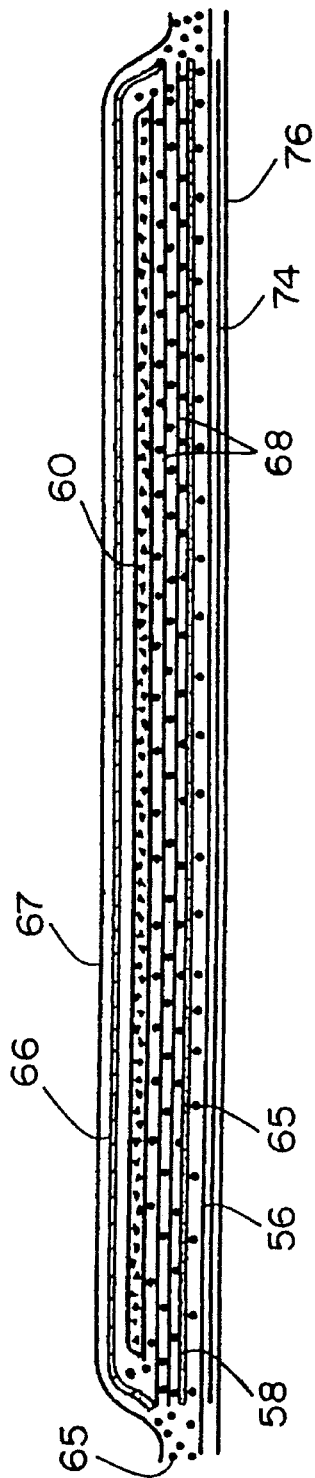
FIG. 7 is a schematic illustration of a cross-sectional view of FIG. 5 along the lines Y—Y.

Referring to FIGS. 5, 6, and 7, a third embodiment of the sanitary napkin 50 is also about 150 mm. to 320 mm. long, about 60 mm. to 120 mm. wide. The sanitary napkin 50 is relatively thin and has a caliper or thickness of less than about 5 millimeters, more desirably less than about 4 millimeters, and most desirably less than about 3 millimeters. The sanitary napkin 50 has a body-facing side 52, a garment-facing side 54, a substantially liquid-impermeable backing sheet or baffle 56, a substantially nonabsorbent, resilient layer 58 and an absorbent means 60.

The resilient layer 58 is made of a flexible, closed cell polyethylene foam material. It is the same type of foam material as used in the first embodiment and is available from the same sources as identified for the first embodiment. The resilient layer 58 is located adjacent to the baffle 56. The absorbent means 60 is located on the opposite side of the resilient layer 58 from the baffle 56. The absorbent means 60 is substantially aligned along the central longitudinal axis Y—Y of the sanitary napkin 50. The resilient layer 58 has a width greater than the width of the absorbent means 60. The resilient layer 58 has a length equal to, and desirably greater than, the absorbent means 60. The resilient layer 58 has a length of at least 60% of the length of the napkin 50.

The baffle 56 is designed to face the inner surface, generally the crotch portion, of an undergarment (not shown). The baffle 56 permits the passage of air or vapor out of the sanitary napkin 50 while blocking the passage of body fluids and liquids. The baffle 18 can be made from micro-embossed polymeric films such as polyethylene or polypropylene, or it can be made from bicomponent films. A preferred material is polyethylene film.

The absorbent means 60 has an overall length which extends at least about 50%, and desirably at least about 75%, of the length of the napkin 15. The absorbent means 60 has a width of less than about 2.5 inches (63.5 mm.), desirably less than about 2 inches (50.8 mm.), more desirably between about 0.5 and 2.0 inches (12.7 mm. and 50.8 mm.), and most desirably about 1.25 inches (31.8 mm.) or 1.50 inches (38.1 mm.) when measured across the central transverse axis Y—Y of the napkin 50. Desirably, the absorbent means 60 has a width which is less than about 60% of the total width of the body-facing side of the sanitary napkin 50 when measured across the narrowest portion of the napkin 50. The total width of the sanitary napkin 50 is measured along an axis, such as axis X—X in FIG. 5, transverse to the longitudinal axis Y—Y of sanitary napkin 50. The total width of the sanitary napkin is the distance from one outer side edge 61 to the opposite outer side edge 63 of the body-facing side of the napkin. Desirably, the width of the napkin spans the width of the labia majora of the user. Arranging the absorbent means 60 substantially in the center, that is, in substantial alignment with the central longitudinal axis Y—Y of the sanitary napkin 50, provides the advantage of placing the absorbent means 60 close to the source of fluid.

The absorbent means 60 has sufficient stiffness to enable the sanitary napkin 50 to resist twisting and "roping", as a result of its stiffness. The absorbent means 60 does not extend the full width of the sanitary napkin 50 in order to enhance comfort to the wearer. The resilient layer 58 has sufficient resilience to resist bunching of the sanitary napkin 50. The combination of the resilient layer 58 and the absorbent means 60 resists both twisting and bunching. The resilient layer 58 is not as stiff as the absorbent means 60 and, for that reason, is arranged to be wider than the absorbent means 60. Desirably the width of the resilient layer 58 is in the range of 60% to 100% of the total width of the sanitary napkin 50.

The absorbent means 60 constitutes the significant absorbing portion of the napkin 50 and has the capability of absorbing at least about 80%, preferably about 90%, and most preferably about 95% of the body fluid deposited on the napkin 50. In terms of amount of body fluid, the absorbent means 60 can absorb at least 10 grams, desirably about 20 grams, and most desirably, about 30 grams or more of body fluid. Thus, the absorbent means 60 is both the primary absorbent and a stiffening means.

On the body-facing side 52 of the sanitary napkin 50, there is a bicomponent cover 62 on the outside of the sanitary napkin 50. Under the cover 62 and adjacent to the cover 62, there is a transfer layer 66. There is no construction adhesive between the transfer layer 66 and the cover 62. In FIGS. 6 and 7, the construction adhesive 65 is represented by a series of dots in various locations and between various layers or components in the sanitary napkin 50.

The bicomponent cover 62 is similar to a bicomponent cover described in U.S. patent application Ser. No. 731,583, now U.S. Pat. No. 5,415,640 filed in the name of Robert E. Kirby et al., entitled "A Bodyside Cover for an Absorbent Article" and assigned to the same assignee as this Patent Application. The bicomponent cover 62 is constructed of two different and distinct materials. The first material 67 of the cover 62 desirably contains a plurality of apertures formed therethrough, while the second material 69 of the cover 62 is desirably nonapertured. The first material 67 is positioned along the central longitudinal axis Y—Y of the sanitary napkin 50 and constitutes the primary fluid-receiving region of the bicomponent cover 62. The sanitary napkin 50 is positioned such that discharge of body fluid from the vaginal orifice is in direct alignment with the upper surface of the first material 67.

In FIG. 6, the second material 69 overlaps a portion of the longitudinal side edges of the first material 67 and is bonded along the side edges by a line of adhesive 65. The second material 69 can be bonded to the first material 67 by a mechanical attachment, an adhesive, an ultrasonic bond, a thermal bond, a pressure bond or a combination of both heat and pressure. Other means of attaching the two materials together can also be used. It should be noted that the first material 67 can be bonded to the second material 69 before the apertures are formed in the first material 67 or vice versa. The bicomponent cover 62 can be constructed off-line and then assembled into the sanitary napkin 50, or it can be constructed in-line.

The second material 69 is secured to the first material 67 and forms a secondary fluid-receiving region of the bicomponent cover 62. The second material 69 is spaced farther away from the point of discharge of body fluid than the first material 67. It should be noted that, even though the second material 69 is designated as the secondary fluid-receiving region of the bicomponent cover 62, it still has the ability to allow fluid to pass down through it. The absorbency rate of the second material 69, which is defined as the amount of time it takes for a material to absorb a certain quantity of fluid, is about equal to or less than the absorbency rate through the first material 67. Accordingly, most of the body fluid, under normal conditions, is designed to pass through the first material 67.

The liquid-permeable cover 62 can also contain a plurality of apertures formed therein and the apertures can be arranged along the longitudinal center line Y—Y, if desired. The apertures will increase the rate at which body fluids can penetrate down into the absorbent means 60. The cover 62 can also be treated with a surfactant to make it more hydrophilic. The surfactant can include topical additions or internally applied materials like polysiloxanes.

The transfer layer 66 is made of an absorbent nonwoven polypropylene spunbond material. In the alternative, the transfer layer 66 may be made of an absorbent nonwoven polypropylene meltblown material, a bonded carded web, or other material having similar properties. Desirably, the transfer layer 66 is aligned along the central longitudinal axis of the sanitary napkin 50 and is sized and configured to correspond to the shape and dimensions of the central absorbent means 60. Desirably also, the transfer layer 66 is slightly longer than the absorbent means 60. A description of a transfer layer 66 is taught in U.S. Pat. No. 4,798,603 issued to Meyer et al. and assigned to the present assignee. This patent is incorporated by reference and made a part hereof. Under the transfer layer 66 is the absorbent means 60. The transfer layer 66 has a width approximately equal to the absorbent means 60. The bicomponent cover layer 62 has a width approximately equal to the width of the sanitary napkin 50 and the cover layer 62 extends out to the periphery of the sanitary napkin 50.

There is a tissue layer 68 that has two plies and is located between the resilient layer 58 and the absorbent means 60. The tissue layer 68 has a width greater than the absorbent means 60. As a result, the tissue layer 68 extends between the cover layer 62 and the resilient layer 58. During use, menses or other body fluid first contacts the first material 67 of the cover 62, then reaches the transfer layer 66, and then reaches the absorbent means 60. The body-facing side of the transfer layer 66 has no adhesive. The garment-facing side of the transfer layer 66 does have adhesive at each end. But, there is no adhesive between the garment-facing side of the transfer layer 66 and the body-facing side of the absorbent means 60. The absorbent means 60 has a body-facing side and a garment-facing side. There is also adhesive 65 on the garment-facing side of the absorbent means 60 between the tissue layer 68 and the absorbent means 60. There is also adhesive 65 between the two plies of the tissue layer 68.

The resilient layer 58 has a body-facing side and a garment-facing side. The baffle 56 is located on the garment-facing side of the resilient layer 58. There is adhesive between the resilient layer 58 and the baffle 56.

If the resilient layer 58 is too thick, the thickness interferes with comfort of the wearer. It has been found that a thin resilient layer 58 is effective if it is adhered or bonded to the baffle 56. Such a resilient layer 58 bonded to the baffle 56 achieves the desired resistance to bunching and yet allows a thinner resilient layer 58 to be used than if the resilient layer 58 were not bonded to the baffle 56. The thinner resilient layer 58 bonded to the baffle 56 provides more comfort to the user than a thicker resilient layer 58. Bonding the film baffle 56 to the resilient layer 58 of foam also facilitates use of a garment adhesive. It is easier and seems to work better to use a garment adhesive on a film baffle 56 than placing the garment adhesive on a resilient layer 58 made of foam.

Thus, bonding the foam layer to the film baffle 56 enhances comfort, achieves a thinner product and is more economical than a thicker layer of foam. It is desirable to use a layer of foam that is 1/8 inch thick or less. More desirably, one should use a layer of foam that is 1/16 inch in thickness or less. Even more desirably, one should use a layer of film that is 1/32 inch or less.

The cover 62 and the baffle 56 extend to the outer periphery of the sanitary napkin 50. At their outer periphery, the cover 62 and the baffle 56 are joined together by adhesive. Desirably, the resilient layer 58 extends in both length and width close to the outer periphery of the sanitary napkin 50, but within the periphery of the sanitary napkin 50. As a result, the size of the resilient layer 58 is slightly less than the size of the cover 62 and the baffle 56, both in width and in length. The two ply tissue layer 68 has a size approximately equal to the size of the resilient layer 58, both in length and in width.

Referring to FIG. 6, the absorbent means 60 is constructed as a laminate comprised of a hydrocolloidal material positioned within a folded hydrophilic material such as an airlaid tissue, the same as described for sanitary napkin 15, the first embodiment.

The first material 67 of the bicomponent cover 62 may be a thermoplastic film, an extrusion-coated nonwoven, or a net material that has openings between the strands or threads due because of its construction. Useful thermoplastic films include polyolefin materials, such as polyethylene, which can be manufactured in various forms. Such films and film making processes are commercially available from the following companies:

Smith & Nephew Plastic, Ltd. Gilberdyke, Brough North Humderside HU 15 2TD United Kingdom Applied Extrusion Technologies, Inc. P.O. Box 582 Middleton, Del. 19709

Fameccanica Fraz Sambuceto I-66020 San Giovanni Teatino Italy

LCL Manufacturing PTE Ltd. 16 Pandan Rd. Singapore 2260

The first material 67 can also be a net, an embossed net, an extruded netting or a net formed from strands of filaments or threads. Examples of covers constructed of netting are taught in U.S. Pat. Nos.: 2,295,439; 2,564,689; 2,900,980; and 4,741,941. These patents are incorporated by reference and made a part hereof. The open spaces between the filaments or threads of the netting serve the same function as the apertures or perforations formed through a thermoplastic film. The first material 67 can also be a foam material having a plurality of apertures formed therethrough.

An extrusion-coated nonwoven includes a laminate film composite and normally refers to a class of composite materials wherein a lower substrate ply is either mechanically, thermally or chemically adhered to an upper film based ply. The substrate may consist of any nonwoven including bonded carded webs, spunbond webs, meltblown webs or cellulose-based tissues. The upper film ply can be an apertured plastic film, a cast continuous film which would be apertured prior to application to the substrate or be a net material.

The first material 67 has a thickness of less than about 2 millimeters and desirably in the range of from about 0.05 to about 2.0 millimeters. The first material 67 can have a three-dimensional profile to give it extra thickness and enhance its functionality. One way to acquire a three-dimensional profile is to emboss the material between the nip of a pair of rollers.

The apertures formed in the first material 67 can vary in size, shape and pattern. The apertures can be arranged in either a systematic, uniform or random pattern. A systematic pattern, with similarly sized apertures, is desirable. The apertures can be formed by mechanically perforating the material, such as by needling or punching, be formed by hot vacuum drawing, or be formed by other methods known to those skilled in the art. The apertures should be formed through the entire thickness of the first material 67. It should be noted that the geometrical shape of the sidewalls of each aperture can vary. For example, the apertures can be round, triangular, square, or irregular in cross-sectional shape. The sidewalls of the apertures can be aligned perpendicularly to the top plane of the first material 67 or they can be slanted at a desired angle.

When forming the apertures in the first material 67, it is possible to form the apertures such that the apex of each extends below the base plane of the first material 67. This configuration will allow the sidewalls of each aperture to contact and penetrate the fibers of an adjacent layer, for example, a cellulose pulp layer or a separation layer. This can be advantageous in providing rapid transfer of body fluid down, into the absorbent or into a separation layer.

In FIG. 6, the first material 67 is shown forming a smaller portion of the exposed surface area of the bicomponent cover layer 62 than the second material 69. The reason for this is that, when the first material 67 is a thermoplastic film and the second material 69 is a nonwoven web, the film is more expensive than the nonwoven web, and therefore it is beneficial to use less of it. Even though the second material 69 occupies a larger portion of the exposed surface area of the bicomponent cover layer 62 than the first material 67, it is possible to have the first material 67 form an equal or larger portion of the bicomponent cover 62, if desired.

The second material 69 of the bicomponent cover layer 62 is preferably a liquid-permeable nonwoven web. The nonwoven web can be a fibrous material formed from fusible polymeric fibers or filaments. The nonwoven web is non-perforated, although a perforated web can be used if desired. The nonwoven web can be formed from any of the following polymers: polyamides, polyesters, polyolefins, polyvinyl acetate, polyvinyl chloride, polyvinyl alcohol, cellulose acetate, viscose, and the like. Suitable materials include polypropylene spunbond and bonded carded webs. An appropriate nonwoven web material should have a uniform web with a denier of about 1.5 or greater. Such a material, commonly referred to as a linear drawn spunbond, is described in U.S. Pat. No. 4,340,563 issued to Appel et al. and is hereby incorporated by reference and made a part hereof.

The baffle 56 has a body-facing side and a garment-facing side. The sanitary napkin 50 also contains two longitudinally-extending strips of garment adhesive 72 and 74 which are attached to the exterior surface, that is, the garment-facing side, of the baffle. The garment adhesive is commercially available from National Starch and Chemical Company, located at 10 Finderne Ave., Bridgewater, N.J. 08807 U.S.A. The strips of garment adhesive 72 and 74 are used to secure the sanitary napkin to the inside of the crotch portion of an undergarment so that it can be properly aligned with the vaginal opening. A peel strip 76 is releasably attached to the garment adhesive strips 72 and 74 and prevents the adhesive from becoming contaminated prior to attachment to the undergarment. The peel strip 76 can be a white Kraft paper coated on one side so that it can be released from a hot melt adhesive. The peel strip 76 is designed to be removed by the ultimate consumer just prior to placement of the sanitary napkin in the undergarment.

Fourth Embodiment

Figure 8:
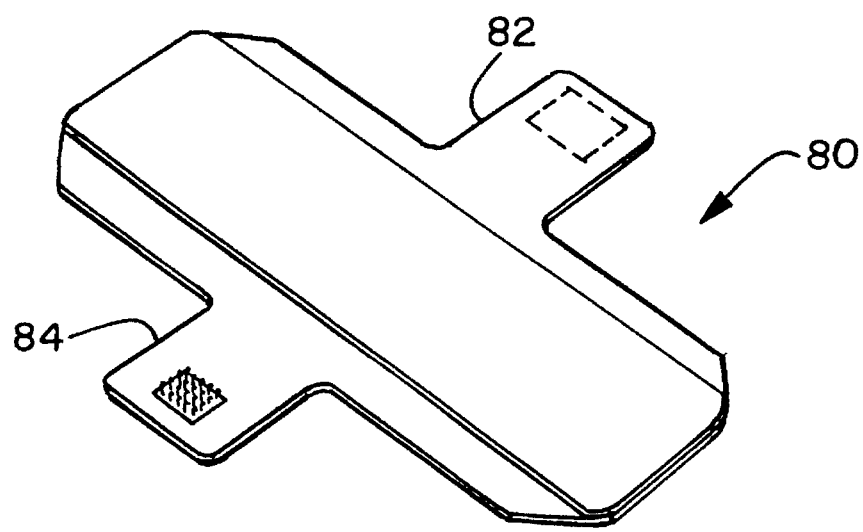
FIG. 8 is a perspective view of a fourth embodiment of the invention.

Referring to FIG. 8, a fourth embodiment of the invention is a sanitary napkin 80 that has a first tab 82 and a second tab 84. One tab is arranged on each side of the sanitary napkin 80. In other respects, the sanitary napkin 80 is similar to the sanitary napkin 50 illustrated in FIGS. 5, 6 and 7. The tabs 82 and 84 are intended to be folded around the undergarment of the user and to increase the attachment of the sanitary napkin 80 to the garment.

Resilient Layer

In the context of this invention, resilience refers to the ability of a material to return or spring back to its original position, an approximately flat position, against the panty, after having been bent or compressed or both. Bending and compression occur during use, as a result of movements of the wearer of the sanitary napkin. This ability of the resilient layer is imparted to the sanitary napkin or other absorbent article. As a result, the entire sanitary napkin has the ability to return to its original position, approximately flat, against the panty.

For the first, second, third and fourth embodiments, it is desirable to select a material for the resilient layer that is substantially non-absorbent and substantially non-wicking. Such a material reduces wicking or other flow of fluid, especially in a transverse direction toward the edge of the sanitary napkin. As a result, such a material reduces any tendency to leak at the sides of the napkin and protects the undergarment and other garments of the user. The resilient layers 19 and 58 may be a foam polymer or it may be another material having properties similar to foam. The material selected for the resilient layer should be one which has desirable resilience properties. The resilience of the material should be substantially unaffected by water and body fluids. Many materials commonly used in absorbent articles, such as pulp and other absorbent materials, do not have sufficient resilience when wet. Wet resilience, that is, resilience when wet, and dry resilience, that is, resilience when dry, are both important.

The resilient layers 19 and 58 provide resistance to bunching. The resilient layers also contribute to stiffness and resistance to twisting. Resistance to bunching is a function of crush resistance force and resilient force. Crush resistance is the ability of a material to resist an applied force, such as a force that tends to crush or bend the material. Resilient force is the force with which the material seeks to return to its original position. The resilient ratio is the ratio of the resilient force to the crush resistance force. To have adequate resistance to bunching, one needs a sufficient resilient force. It is desirable to have this sufficient resilient force in a material that does not have too high of a crush resistance, to insure comfort. Thus a certain minimum resilient ratio is desirable, to be able to deliver a sufficient resilient force to resist bunching without having too high of a crush resistance.

A measure of resilient ratio is rebound resilience, as defined by the American Society for Testing Materials (ASTM) of 1916 Race Street, Philadelphia, Pa. 19103, U.S.A. This is the ratio between the output and input energy of a gravity-activated mass which impacts the test piece. See ASTM Publications D 3575-84, D 3574-86, and D 1054-87. All of the foregoing ASTM publications are incorporated herein by reference and made a part hereof. Desirable materials for use in this invention will have a rebound resilience of at least about 25%.

Crush resistance may be measured by an ASTM Circular Bend Flex Test, as described in ASTM publication D 4032-82. For the purpose of this invention, the plunger described in ASTM D 4032-82 has been modified to have a smaller diameter of 6.25 mm., an end tip radius of 2.97 mm. and a needle point extending 0.88 mm. from the end of the tip. The needle has a 0.33 mm. base diameter and a point having a radius of less than 0.5 mm.

For materials that have similar resilient ratios, resistance to bunching is indicated by this Circular Bend Flex Test. The polyethylene foam material that we have called out in the foregoing Detailed Description has a resilient ratio of about 50%, as indicated by a literature rebound resilience of 50%, listed in Encyclopedia of Polymer Science and Engineering, Vol. 3, pp. 6 and 7, John Wiley and Sons publishers, New York, N.Y., U.S.A., 1985. For this material, a desirable range of crush resistance to provide the desired level of resistance to bunching is indicated by a Circular Bend Flex in the range of from about 9 to about 42 grams, desirably in the range of from about 24 to about 42 grams, more desirably about 35 grams.

A useful class of resilient materials for this invention is foams such as cellular plastics. These cellular plastics have an apparent density which is substantially lower than that of the base polymer (plastic) which is made possible by the presence of numerous cells of gas (air) disposed throughout its mass. Foams are two-phase gas-solid systems that have a supporting solid lattice of polymer or rubber cell walls that are continuous throughout the structure.

The gas (air) phase in a resilient foam is usually distributed in void pockets often called cells. Open cell foams contain interconnected cells where the gas (air) can pass from one cell to another. Closed cell foams contain cells that are discrete from each other such that the gas phase of each is held independently by each cell that are sealed by thin walls of polymer.

The American Society for Testing and Materials (ASTM) classifies foamed plastics as either rigid or flexible. A flexible foam which is most preferred for this invention is one that does not rupture when a 20×2.5×2.5 cm piece is wrapped around a 2.5 cm mandrel at a uniform rate of 1 lap/5 seconds at 15–25 degrees Centigrade. Rigid foams which are not most preferred for this invention are those that do rupture under this test, unless they are modified to make them flexible through such means as scoring or embossing.

Foamed plastics can be prepared by many means. The expansion process is that of expanding a fluid polymer phase to a low density cellular state and then "freezing" the polymer structure by curing or through cooling of the liquid polymer.

The extrusion process for producing resilient foams uses physical stabilization in a decompression expansion process. This process uses a blowing agent blended into the molten polymer that is extruded under pressure. This solution of polymer and blowing agent is forced out through a die opening on to a moving belt at normal room temperature and pressure. This reduction in pressure causes the blowing agent to vaporize resulting in expansion of the polymer. The polymer is allowed to cool during expansion such that enough structural strength is obtained for the required density and dimensional stability. Freezing of the structure or stabilization of the polymer structure is a result of the polymer phase cooling to a point below its glass transition temperature. Cooling comes mainly from three areas: (1) the vaporization of the blowing agent, (2) gas expansion, and (3) heat loss to the environment.

Polyolefin foams made with base polymers of polyethylene and polypropylene are prepared by both molding and extrusion processes. It is desirable for these embodiments to use low density polyethylene foam products which are prepared by an extrusion technique using a gaseous blowing agent. Other methods of producing cellular plastics include leaching out solid or liquid materials that have been dispersed in a polymer, sintering small particles, and dispersing small cellular particles in a polymer.

Other methods of generating the cellular structures are by dispersing gas (or solid) in the fluid state and stabilizing this cellular state, or by sintering polymer particles in a structure that contains a gas phase.

Chemical stabilization process is a common used method used to produce resilient foams. Condensation polymers are more suitable for foaming by this process than for vinyl polymers because of the fast yet controllable curing reactions and the absence of atmospheric inhibition. Polyurethane based foams are made by this process. This is not the most desirable foam for these embodiments due to extractables and long term aging and discoloration of polyurethanes foamed products.

Decompression expansion foam processes are most preferred for making the foam used in these embodiments. By using a physical stabilization process, cellular polystyrene, cellulose acetate, polyolefins, or poly(vinyl chloride) can be manufactured for use in these embodiments.

Examples of other materials that may be used for the resilient layers 19 and 58 are: silicone, polyurethane, polypropylene, latex and pulp. If the material is not substantially non-absorbent, desirably it should be treated to make it substantially non-absorbent.

Zones of Thickness, Stiffness and Absorbency

Referring to FIGS. 2 and 6, the sanitary napkins 15 and 50 each have at least two zones which extend longitudinally, that is, parallel to longitudinal axis Y—Y: a central absorbent zone 102 and 122 and a peripheral zone 106 and 126. Desirably, the napkins 15 and 50 also have an adjacent zone 104 and 124 between the central absorbent zone and the peripheral zone. Desirably, there are two peripheral zones, one on each side of the napkins 15 and 50 and two adjacent zones, one on each side of the napkin. The central absorbent zones 102 and 122, the adjacent zones 104 and 124 and the peripheral zones 106 and 126 are all at least 60% of the total length of the napkins 15 and 50.

The sanitary napkins 15 and 50 are thickest, stiffest, and most absorbent in their central absorbent zones 102 and 122 where the absorbent means 20 and 60 are located. They are less thick, less stiff, and less absorbent in the adjacent zones 104 and 124 and are least thick, least stiff, and least absorbent in the peripheral zones 106 and 126. As a result, the sanitary napkins 15 and 50 are thinner in their adjacent zones 104 and 124 and peripheral zones 106 and 126 than most sanitary napkins. Also, as a result, the sanitary napkins 15 and 50 are softer in their peripheral zones 106 and 126 than most sanitary napkins, which enhance comfort. The sanitary napkins 15 and 50 have a finished peripheral edge which visually communicates to the user that fluid is not likely to reach the edges, especially the side edges, because the main absorbent does not extend to the side edges.

The stiffness of the central absorbent zones can be obtained by making the central absorbent zone thicker; by constructing it out of several layers, by using stiffer materials, by changing the basis weight or by placing another layer of material vertically adjacent to it. The central absorbent zone has a Gurley stiffness of at least about 500 milligrams, and desirably higher. See Tables 1 and 2.

Referring to FIG. 2, the central absorbent zone in thickness, that is, in cross section, includes: the cover layer 22, the transfer layer 4, the first tissue layer 28, the absorbent means 20, the second tissue layer 30, the resilient layer 19, the baffle 18, the garment adhesive 36, the peel strip 39, and construction adhesive 26 between various layers. The absorbent means 20 is a component within the central absorbent zone 102. The central absorbent zone 102, like the absorbent means 20, has a central longitudinal axis that is coincident with the central longitudinal axes Y—Y of the sanitary napkin 15. The width of the central absorbent zone 102 is equal to the width of the absorbent means 20.

Referring to FIG. 6, the central absorbent zone of sanitary napkin 50 includes the following layers: the bicomponent cover layer 62, the transfer layer 66, the absorbent means 60, the two ply tissue layer 68, the resilient layer 58, the baffle 56, the garment adhesive, the peel strip, and construction adhesive between the various layers. The absorbent means 60 is a component within the central absorbent zone 122. The central absorbent zone 122, like the absorbent means 60, has a central longitudinal axis that is coincident with the central longitudinal axes Y—Y of the sanitary napkin 50. The width of the central absorbent zone is equal to the width of the absorbent means.

Referring to FIG. 2, the adjacent zones 104 include the following layers: the cover layer 22, the first tissue layer 28, the second tissue layer 30, the resilient layer 19, the baffle 18, the garment adhesive 36, and the peel strip 39, and construction adhesive 26 between the various layers. The adjacent zone does not include the absorbent means 20 and the transfer layer 24.

Referring to FIG. 6, the adjacent zone 124 likewise includes the following layers: the cover layer 62, the two ply tissue layer 68, the resilient layer 58, the baffle 56, the garment adhesive, the peel strip, and construction adhesive between the various layers. The adjacent zone 124 does not include the absorbent means 60 and the transfer layer 66.

Referring to FIG. 2, the peripheral zone 106 includes the following layers: the cover layer 22, the baffle 18 and construction adhesive 26 between the cover layer 22 and the baffle 18. The peripheral zone 106 may also include a small portion of the outer side edge of the resilient layer 19.

Referring to FIG. 6, the peripheral zone 126 of sanitary napkin 50 includes the following layers: cover layer 62, baffle 56 and construction adhesive 66 between the cover layer 62 and the baffle 56. The peripheral zone 126 may also include a portion of the outer edge of the tissue layer 68 and the resilient layer 58, and adjacent construction adhesive 65.

Stiffness Testing

The ability of certain layers of a sanitary napkin to resist an applied bending force, known as pad stiffness, is determined by measuring the amount of force required to bend a rectangular composite sample cut from the sanitary napkin that includes all layers excluding the peel strip. The force needed to bend each sample is measured using a Gurley Model 4171-d Digital Stiffness Tester which along with weights and precalibration strips are available through Teledyne Gurley, Troy, New York, U.S.A. The Gurley stiffness test procedure is modeled after the Technical Association of the Pulp and Paper Industry (TAPPI) method T 543 pm-84. The Gurley Digital Stiffness Tester is an instrument consisting of a balanced vane, which is center-pivoted, and to which a variety of weights can be added below its pivot point. The vane moves freely to accommodate testing in both left and right directions which would be analogous to upward and outward body flexing of the samples.

There is a two part calibration for the Gurley Stiffness Tester. The first calibration is done to ensure that the "Vane" pendulum is swinging according to specification against a known material (i.e., a brass strip). The Gurley instrument is calibrated following the Gurley Digital Stiffness Tester Instruction Manual to within 5% variation with a 50.8 mm. wide by 25.4 mm. long precalibrated Brass Calibration Strip, Gurley part no. 31644. The second calibration is done to ensure that the internal electronic calculations and conversions are accurate.

The samples cut from each sanitary napkin are 12.7 mm.±0.4 mm. wide by 25.4 mm.±0.4 mm. long. Each sample overlaps the top of the Gurley vane by 6.4 mm. During a test, the sample is moved against the top edge of the vane until the sample bends and the vane releases contact with the bottom edge of the sample. The point of release is measured by an electronic optical encoder which provides a greater degree of accuracy over the earlier model Gurley Stiffness Tester as was used in TAPPI T 543 pm-84. The electronic optical encoder also displays the result on the digital readout. The readout continuously displays readings from tests performed in both the left and right directions. The Gurley Model 4171-d also computes automatically through an internal microprocessor and displays the average of left and right bending stiffness data after each measurement. The average reading is then converted by this Gurley instrument into milligrams of Gurley stiffness relative to a sample size of 24.5 mm. wide by 76.2 mm. long.

The Gurley Stiffness Tester should be prepared as follows. The required weight is attached and the base of the instrument is levelled by adjusting the leveling screw until the level's bubble is centered and the pendulum's pointer is indicating zero. The switches are set to correspond to the weight being used, the weight's position on the pendulum, the width of the specimen being tested, and the length of the specimen. For example: if a 25.4 mm.×12.7 mm. specimen is tested with the 5 gm weight in the 25.4 mm. slot, the switches would be set as follows:

Weight=5 gm

Weight Position=1 inch

Width=0.5 inch

Length=1 inch

The test procedure to be performed is as follows:

1. Center the specimen strip over the pendulum such that exactly 6.4 mm. (0.25 inches) overlaps the top of the pendulum and exactly 6.4 mm. (0.25 inches) will be held in the jaws.
2. Select an appropriate weight and a hole to give a reading between 2 and 6 on the scale. NOTE: The specimen should be brought to an approximate contact with the pendulum vane before applying force to avoid oscillation in the early stages.
3. Press the System Reset button. The display must read 00-000-00.
4. Press the Motor—Direction switch to cause the clamp arm to press the specimen against the pendulum.
5. Repeat step 4 in the opposite direction to establish both a left scale reading, a right scale reading, and an average reading.
6. Record the average scale reading.
7. Press the Select Button to attain the milligram calculation and record.
8. Repeat steps 1 through 7 for each specimen.

The following procedure was used to obtain samples for Gurley stiffness testing. A set of samples was cut from five sanitary napkins of the types shown in the Tables. Each sample measured 12.7 mm. by 25.4 mm. Tables 1 through 16 show comparative data between sanitary napkins of the invention described herein and commercially available sanitary napkins which are relatively thin in caliper. In the Tables, K-C refers to Kimberly-Clark Corporation of Dallas, Tex., U.S.A. Invention A and Invention B refer to sanitary napkins 50 of the type described herein as the Third Embodiment. Invention H, J, M and W refer to sanitary napkins 15 of the type described herein as the First Embodiment. The K-C Ultra Thin Pad with Pulp is described in U.S. patent application Ser. No. 556,694, now U.S. Pat. No. 5,248,309 filed in the name of Serbiak et al. and assigned to Kimberly-Clark Corporation. P&G refers to the Procter & Gamble Company of Cincinnati, Ohio U.S.A. The K-C Ultra Thin Pad with Pulp and the P&G Whisper Excel product with wings, shown in the Tables, are commercially available sanitary napkins. The commercially available sanitary napkins shown in the Tables do not have the same construction, layers and zones as the sanitary napkins 15 and 50 of the present invention. Samples were cut from comparable locations in the commercially available napkins as much as possible to provide the comparison shown in the Tables.

Figure 9:
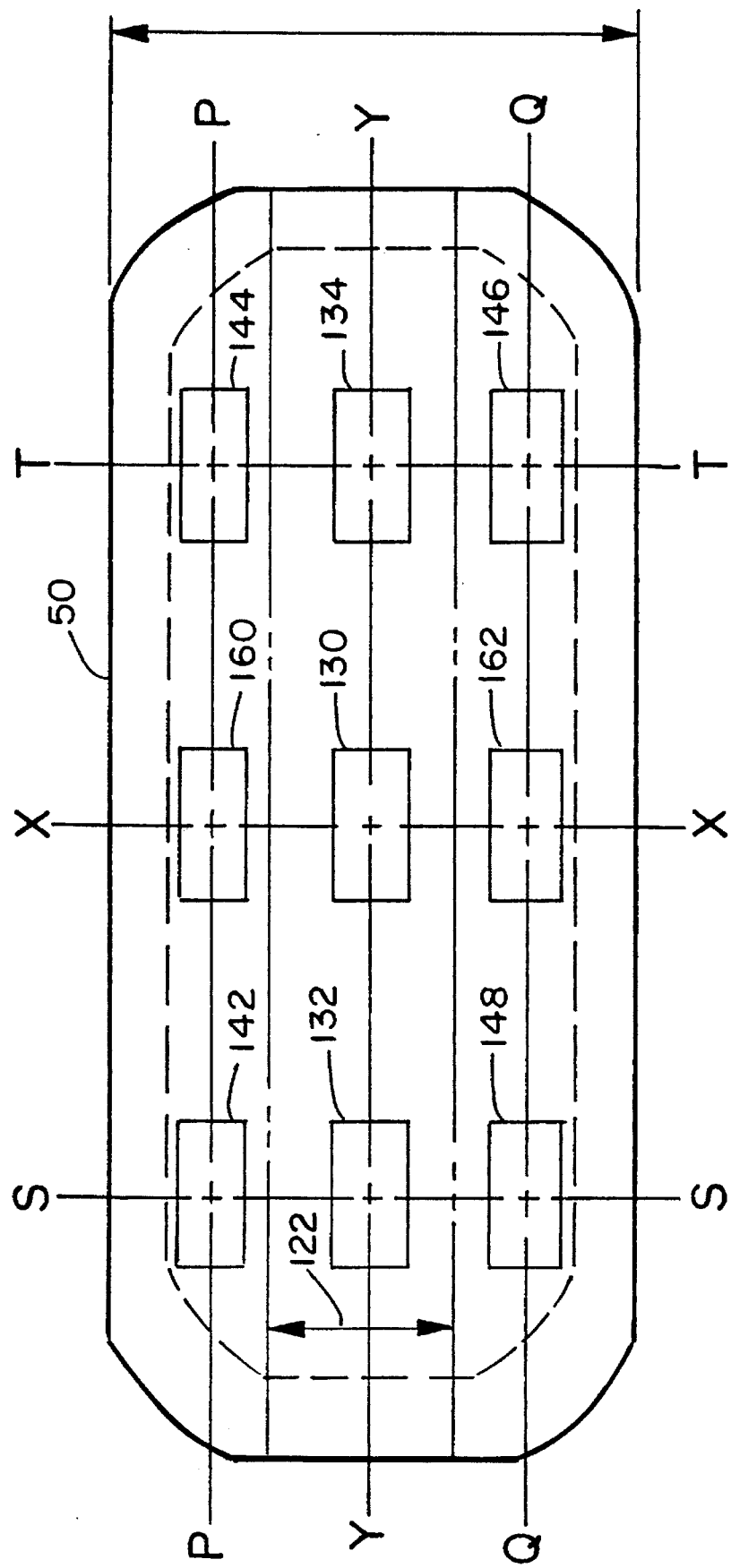
FIG. 9 is a top plan view of the third embodiment shown in FIG. 5, showing segments in the machine direction for the central absorbent zone and the adjacent zones.
Figure 10:
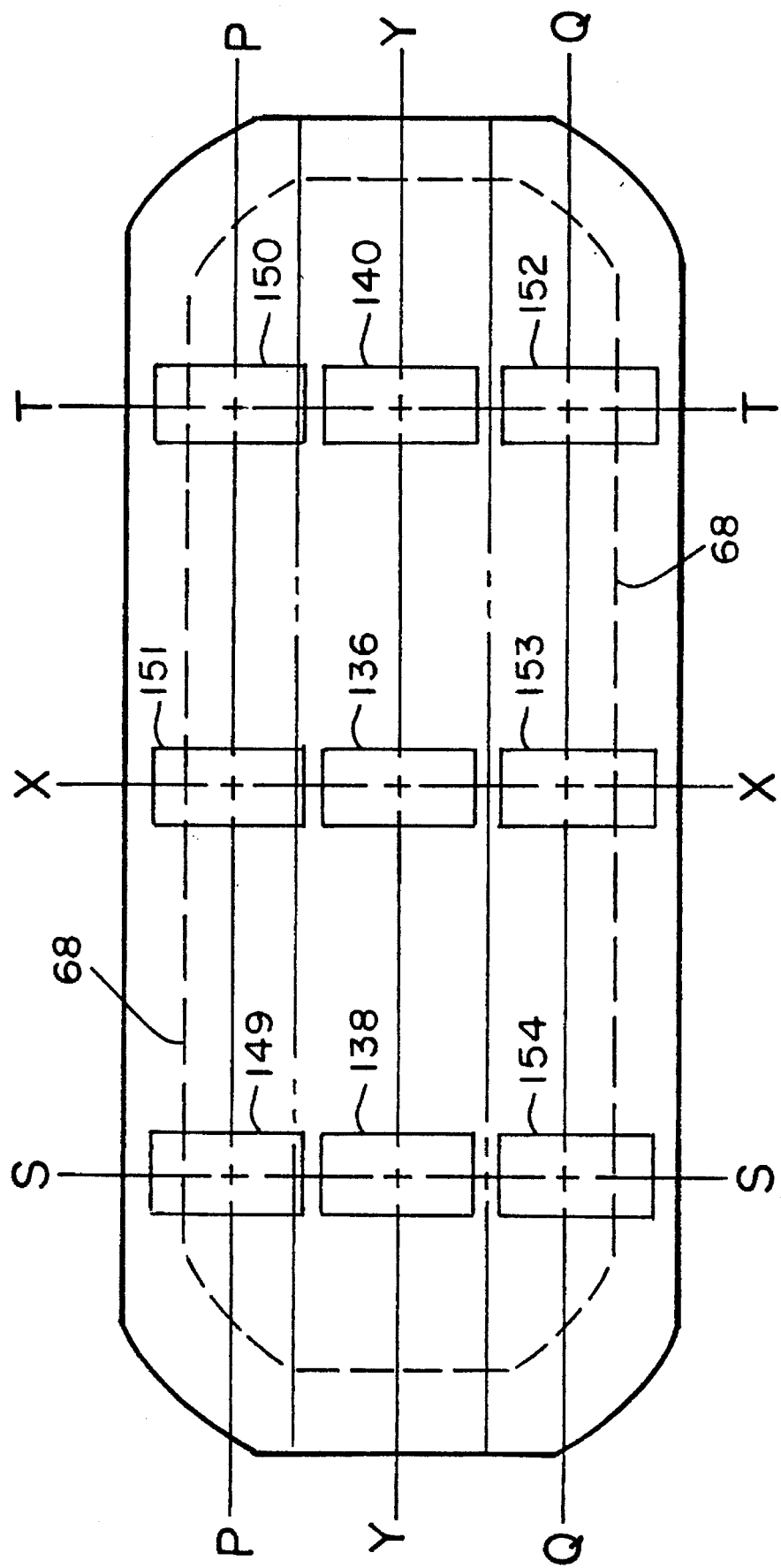
FIG. 10 is also a top plan view of the third embodiment shown in FIG. 5, showing segments in the transverse direction for the central absorbent zone and the adjacent zones.
Figure 11:
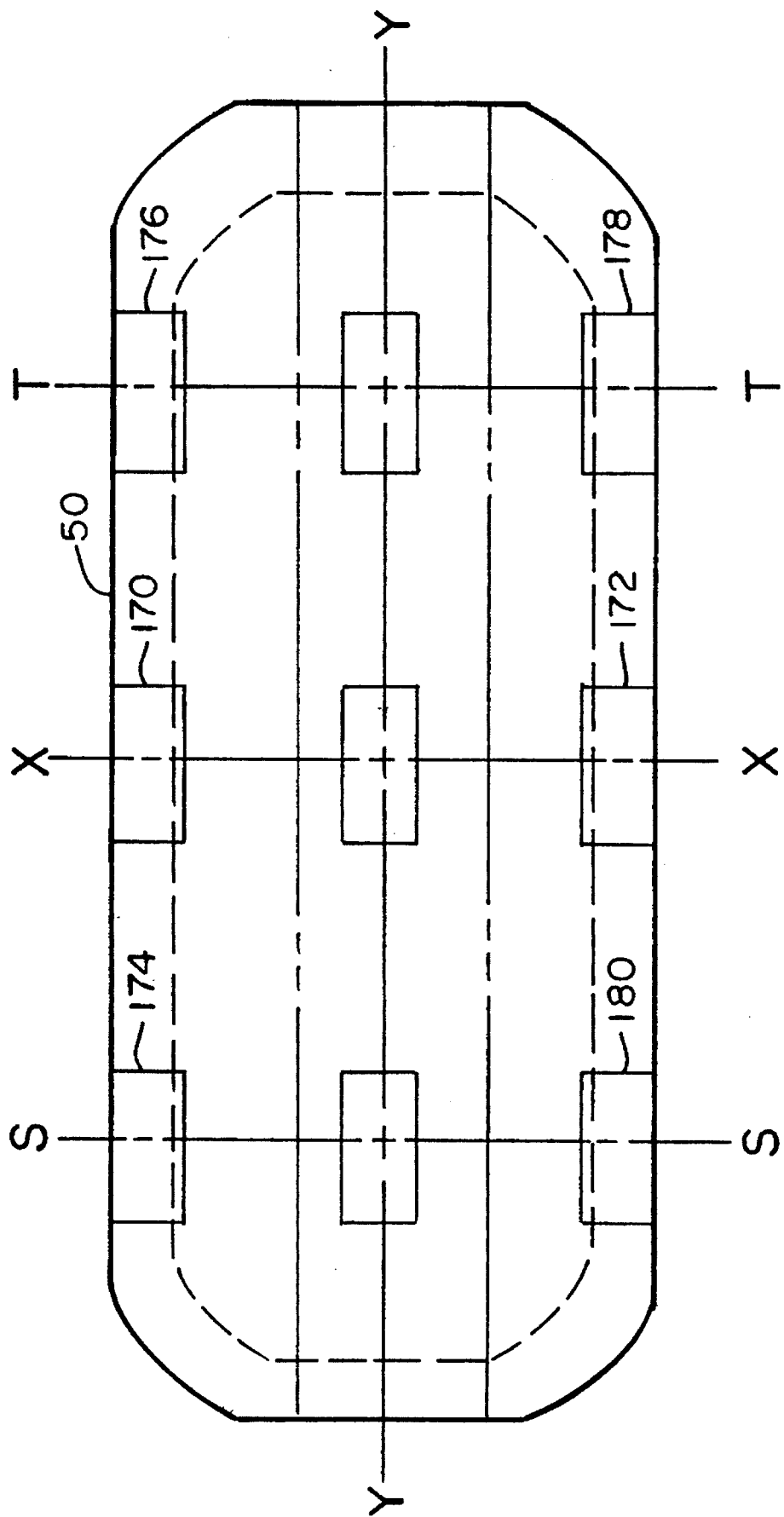
FIG. 11 is also a top plan view of the third embodiment shown in FIG. 5, showing segments in the machine direction in the central absorbent zone and in the peripheral zones.
Figure 12:
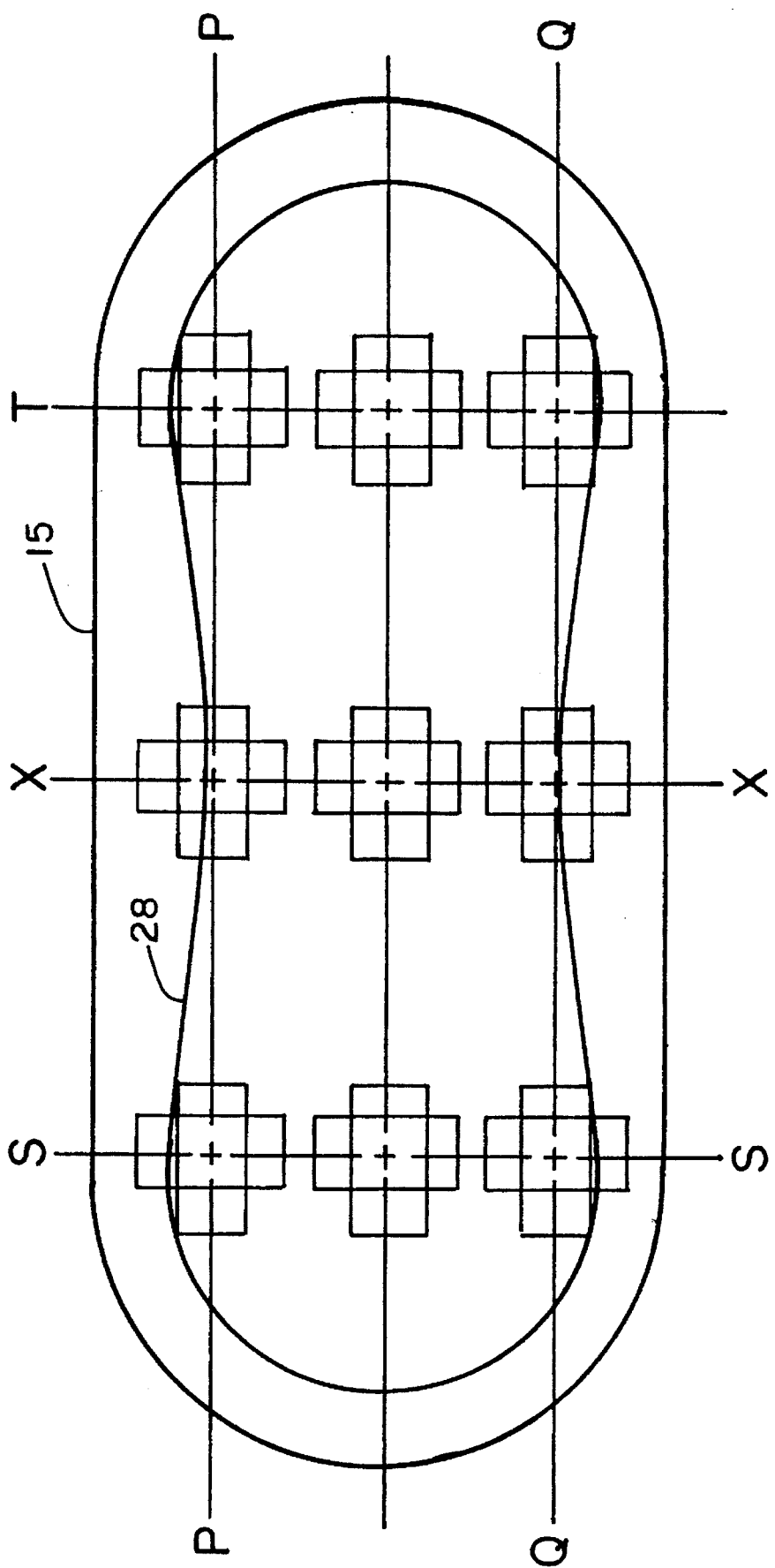
FIG. 12 is a top plan view of the first embodiment shown in FIG. 1, showing segments in both the machine direction and the transverse direction.
Figure 13:
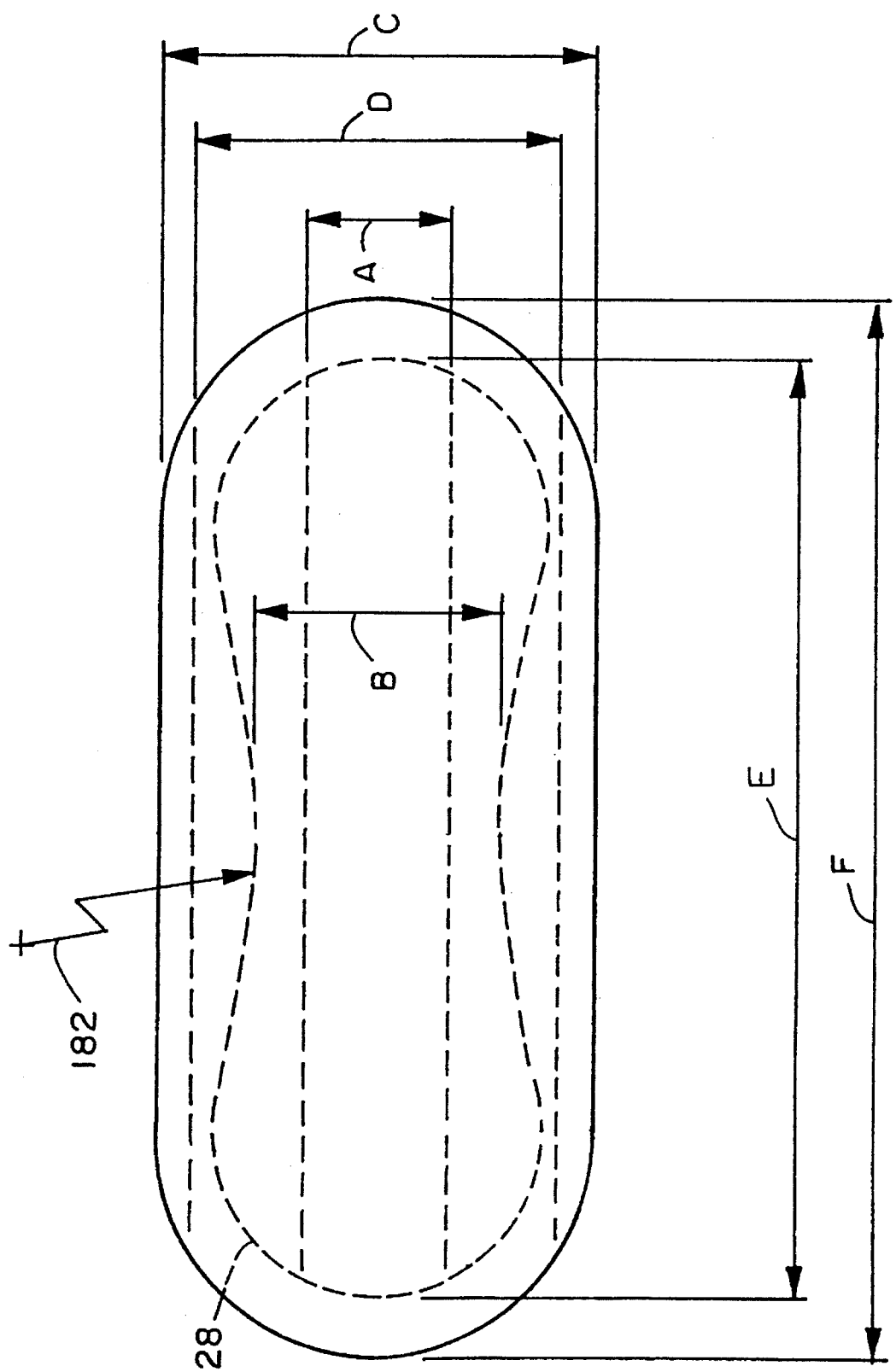
FIG. 13 is a top plan view of the first embodiment shown in FIG. 1.

FIGS. 9, 10, and 11 show where samples were cut from napkins 50, the Third Embodiment. FIG. 12 shows where samples were cut from napkins 15, the First Embodiment. FIG. 13 shows the location of certain measurements. The longitudinal centerline Y—Y and the transverse centerline X—X of each napkin were identified. The peel strip was removed and the garment adhesive was dusted with talc or corn starch. Referring to FIG. 9, a sample 130 measuring 12.7 mm.×25.4 mm. was cut in the machine direction from each napkin 50 at the intersection of the two centerlines Y—Y and X—X. The machine direction referred to in Tables 1, 3, 4, 5, 6, 7, 8, 9, 10, 11, 12, 13, and 14 corresponds to the longitudinal direction of the napkin, i.e. axis Y—Y. The transverse direction referred to in Table 2 corresponds to the transverse axis X—X of the napkin 50. Two additional samples 132 and 134, each measuring 12.7 mm.×25.4 mm., were cut in the machine direction along the longitudinal centerline. The two additional samples 132 and 134 were cut about 63.5 mm. in front of and behind the first sample 130. All samples from each napkin were cut and handled carefully so as not to affect the sample stiffness. Such samples included the central absorbent means 20 plus segments from the other layers present at the locations where the samples were taken, that is, from the central absorbent zone 122. The Gurley stiffness was measured for each sample and the values were recorded in Table 1 as the stiffness of the central absorbent zone 122 in the machine direction.

Referring to FIG. 9, we then identified parallel planes S and T. Planes S and T are parallel to the transverse centerline X—X and are 63.5 millimeters in front of and behind the transverse centerline X—X. Next we identified parallel planes P—P and Q—Q. Planes P—P and Q—Q are parallel to longitudinal centerline Y—Y and at a distance of (C/4+ 6.4 mm.) from centerline Y—Y. C is a measurement of the total width of the napkin 50 at its narrowest dimensions between planes S and X and planes T and X (shown in FIGS. 11 and 12). We then identified the points of intersection for planes P—P, Q—Q, S—S, and T—T. At the intersection of planes P—P and S—S, we cut sample 142. At the intersection of planes P—P and T—T, we cut sample 144. At the intersection of planes Q—Q and T—T, we cut sample 146. At the intersection of planes Q—Q and S—S, we cut sample 148. The four samples 142, 144, 146 and 148 each measured 25.4 millimeters×12.7 millimeters. Such samples are in the offset adjacent zone 124 and include the resilient layer 58, but not the absorbent means 60. Such samples are offset from transverse axis X—X. The Gurley stiffness of the samples from the adjacent zone were measured and recorded in Table 4 as the stiffness of the offset adjacent zones in the machine direction.

Referring to FIG. 9, we also identified the points of intersection for planes P—P, Q—Q, X—X, and Y—Y. At the intersection of planes P—P and X—X, we cut sample 160. At the intersection of planes Q—Q and X—X, we cut sample 162. The two samples 160 and 162 each measured 25.4 millimeters×12.7 millimeters. Such samples are in the center adjacent zones and include the resilient layer 58, but not the absorbent means 60. The Gurley stiffness of the samples from the center adjacent zones were measured and recorded in Table 3 as the stiffness of the center adjacent zone in the machine direction.

Referring to FIG. 10, from another set of five napkins 50 another sample 136 measuring 12.7 mm. and 25.4 mm. was cut in the transverse direction from each napkin at the intersection of the two centerlines Y—Y and X—X. Two additional samples 138 and 140, each measuring 12.7 mm.× 25.4 mm., were cut in the transverse direction along the longitudinal centerline. The two additional samples 138 and 140 were cut about 63.5 mm. in front of and behind the first sample. All samples from each napkin were cut and handled carefully so as not to affect the sample stiffness. Such samples included the central absorbent means 20 plus segments from the other layers present at the locations where the samples were taken, that is, from the central absorbent zone 122. The Gurley stiffness was measured for each sample and the values were recorded in Table 2 as the stiffness of the central absorbent zone in the transverse direction.

Referring to FIG. 10, we also identified parallel planes S and T. Planes S and T are parallel to the transverse centerline X—X and are 63.5 millimeters in front of and behind the transverse centerline X—X. Next we identified parallel planes P—P and Q—Q. Planes P—P and Q—Q are parallel to longitudinal centerline Y—Y and at a distance of (C/4+ 6.4 mm.) from centerline Y—Y. C is a measurement of the total width of the napkin 50. We then identified the points of intersection for planes P—P, Q—Q, S—S, and T—T. At the intersection of planes P—P and S—S, we cut sample 149 in the transverse direction. At the intersection of planes P—P and T—T, we cut sample 150 in the transverse direction. At the intersection of planes Q—Q and T—T, we cut sample 152 in the transverse direction. At the intersection of planes Q—Q and S—S, we cut sample 154 in the transverse direction. The four samples 149, 150, 152, and 154 each measured 25.4 millimeters×12.7 millimeters. Such samples are in the offset adjacent zone 124 and include the resilient layer 58, but not the absorbent means 60. Such samples are offset from transverse axis X—X. The Gurley stiffness of the samples from the adjacent zone were measured as the stiffness of the offset adjacent zones in the transverse direction.

Referring to FIG. 10, we also identified the points of intersection for planes P—P, Q—Q, X—X, and Y—Y. At the intersection of planes P—P and X—X, we cut sample 151 in the transverse direction. At the intersection of planes Q—Q and X—X, we cut sample 153 in the transverse direction. The two samples 151 and 153 each measured 25.4 millimeters×12.7 millimeters. Such samples are in the center adjacent zones and include the resilient layer 58, but not the absorbent means 60. The Gurley stiffness of the samples from the center adjacent zones were measured as the stiffness of the center adjacent zone in the transverse direction.

Referring to FIG. 11, four additional points, two on each side of the sanitary napkin 50 were identified on the planes S—S and T—T on the outer longitudinal sides of the napkin. Samples 174, 176, 178 and 180 were cut in the machine direction from each of these points. Such samples did not include the central absorbent means 60 and included only a small portion of the resilient layer 58 and segments from the other layers present where the samples were taken. The Gurley stiffness of each sample is measured and recorded in Table 6 as the stiffness of the offset peripheral zones of the napkin 50 in the machine direction. The average for the stiffness of the offset peripheral zones was calculated and recorded as the "average stiffness of the peripheral zones" of the napkin. The average stiffness of the offset peripheral zones was then subtracted from the average stiffness of the central absorbent zone of the napkin and is recorded in Table 8 as the difference in stiffness between the central absorbent zone and the offset peripheral zones of the napkins in the machine direction.

Referring to FIG. 11, two additional points, one on each side of the transverse centerline X—X, were identified on the outer longitudinal sides of the napkin 50. Samples 170 and 172 were cut in the machine direction from each of these points. Such samples did not include the central absorbent means 20 and included only a small portion of the resilient layer 58 and segments from the other layers present where the samples were taken. The Gurley stiffness of each sample 170 and 172 was measured and recorded in Table 5 as the stiffness of the center peripheral zones of the napkin in the machine direction. The average for the stiffness of the center peripheral zones was calculated and recorded as the "average stiffness of the center peripheral zones" of the napkin. The average stiffness of the center peripheral zones was then subtracted from the average stiffness of the central absorbent zone of the napkin and is recorded in Table 7 as the difference in stiffness between the central absorbent zone and the center peripheral zones of the napkin in the machine direction.

The average of the values of the stiffness of the central absorbent zone was calculated and recorded as the "average stiffness of the central absorbent zone" for the napkin. The average of the values of the stiffness of the adjacent zones was calculated and recorded as the "average stiffness of the adjacent zones" for the napkin. The "average stiffness of the central absorbent zone" was then divided by the "average stiffness of the adjacent zones" and is reported as the stiffness ratio of the central absorbent zone to the adjacent zone. Referring to FIGS. 12 and 13, sanitary napkin 15 has tissue layers 28 and 30 that have an hourglass shape 182. Samples were cut from napkins 15 in a manner similar to that previously described for FIGS. 9 and 10. Referring to FIG. 13, the width of the absorbent zone is A. The width of the tissue layers 28 and 30 along the transverse axis X—X is B. Dimension B is the minimum width of the tissue layers 28 and 30. The total width of the napkin is C at its narrowest dimensions between planes S and X and planes T and X (shown in FIGS. 11 and 12). Dimension D is the width of the resilient layer. Dimension E is the length of the tissue layers. Dimension F is the length of the napkin.

Table 1 shows the stiffness of samples or segments cut from the central absorbent zone in the machine direction for sanitary napkins of the present invention and the stiffness of samples from comparable locations for other sanitary napkins available commercially. For the present invention, the stiffness of the central absorbent zone in the machine direction is in the range of from about 477 milligrams (mg.) to about 3067 mg. Desirably, it is in the range of from about 782 mg. to about 2526 mg. Desirably also, it should be above about 477 mg.

Table 2 shows the stiffness of samples or segments cut from the central absorbent zone in the transverse direction for sanitary napkins of the present invention and the stiffness of samples from comparable locations for sanitary napkins available commercially. For the present invention, the stiffness of the central absorbent zone in the transverse direction is in the range of from about 342 mg. to about 2445 mg. Desirably, it is in the range of from about 494 mg. to about 1647 mg. Desirably also, it should be above about 494 mg.

Table 3 shows the stiffness of samples or segments cut from the center adjacent zones in the machine direction for sanitary napkins of the present invention and the stiffness of samples from comparable locations for other sanitary napkins available commercially. Such samples 160 and 162 from the center adjacent zones are shown in FIG. 9 at the intersection of plane P—P and transverse axis X—X and at the intersection of plane Q—Q and transverse axis X—X. For the present invention, the stiffness of the center adjacent zones is in the range of from about 99 mg. to about 345 mg. Desirably, it is in the range of from about 131 mg. to about 297 mg.

Table 4 shows the stiffness of samples or segments cut from the offset positions in the adjacent zones in the machine direction for sanitary napkins of the present invention and the stiffness of samples from comparable locations for other sanitary napkins available commercially. Such samples are shown in FIG. 9 that is, sample 142 at the intersection of plane P—P and S—S; sample 144 at the intersection of plane P—P and plane T—T; sample 146 at the intersection of plane Q—Q and plane T—T and sample 148 at the intersection of plane Q—Q and S—S. For the present invention, the stiffness of the offset adjacent zones is in the range of from about 97 mg. to about 411 mg. Desirably, it is in the range of from about 121 mg. to about 317 mg.

Table 5 shows the stiffness of samples cut from the center of the peripheral zones in the machine direction, that is, samples 170 and 172 shown in FIG. 11 along the transverse axis X—X at each side of the napkin for sanitary napkins of the present invention and the stiffness of samples from comparable locations for other sanitary napkins available commercially. For the present invention, the stiffness of the center peripheral zones is in the range of from about 28 mg. to about 127 mg. Desirably, it is in the range of from about 52 mg. to about 78 mg.

Table 6 shows the stiffness of samples or segments cut from the peripheral zones at their offset positions in the machine direction, that is, samples 174 and 176 along the plane S—S at each side of the napkin and samples 178 and 180 along the plane T—T at each side of the napkin. For the present invention, the stiffness of the offset peripheral zones is in the range of from about 30 mg. to about 115 mg. Desirably, it is in the range of from about 70 mg. to about 79 mg.

Table 7 shows the difference between the average stiffness of the central absorbent zone in the machine direction, shown in Table 1, and the average stiffness of the adjacent zones in the machine direction from Table 3 for center adjacent zones, and from Table 5 for the center peripheral zones for sanitary napkins of the present invention and differences in average stiffness for comparable locations for other sanitary napkins available commercially. "N.D." in the Tables means no data is available.

Table 8 shows the difference in average stiffness in the machine direction between the center adjacent zones shown in Table 3 and the center peripheral zones shown in Table 5.

The stiffness of the center adjacent zones is represented by samples 160 and 162 in FIG. 9. The stiffness of the center peripheral zone is represented by samples 170 and 172 in FIG. 11.

Table 9 shows the difference in average stiffness in the machine direction between the central absorbent zones and offset zones, both the offset adjacent zones and the offset peripheral zones. The offset adjacent zones are represented by samples 142, 144, 146, and 148 in FIG. 9 and the average stiffness is shown in Table 4. The offset peripheral zones are represented by samples 174, 176, 178 and 180 in FIG. 11 and the average stiffness is shown in Table 6. For the present invention, the difference in average stiffness between the central absorbent zone and offset adjacent zones is in the range of from about 632 mg. to about 2293 mg. The difference in average stiffness between the central absorbent zone and the offset peripheral zones is in the range of from about 953 mg. to about 2456 mg.

Table 10 shows the difference in average stiffness between the offset adjacent zones, that is, represented by samples 142, 144, 146, and 148 in FIG. 9 and shown in Table 4; and the offset peripheral zones represented by samples 174, 176, 178, and 180 in FIG. 11 and shown in Table 6. For the present invention, the difference in average stiffness between the offset adjacent zones and the offset peripheral zones is in the range of from about 50 mg. to about 162 mg.

Table 11 shows the ratio of the average stiffness of the central absorbent zones, represented by samples 130, 132, and 134 in FIG. 9, to the average stiffness of the center adjacent zones, represented by 160 and 162 in FIG. 9 and shown in Table 3 and to the center peripheral zones, represented by samples 170 and 172 in FIG. 11 and shown in Table 5. The ratio of the average stiffness of the central absorbent zone to the average stiffness of the center adjacent zones is in the range of from about 3.7:1 to about 10.3:1. The ratio of the average stiffness of the central absorbent zone to the average stiffness of the center peripheral zones is in the range of from about 14.5:1 to about 32.4:1.

Table 12 shows the ratio of the average stiffness of the central adjacent zones, represented by samples 160 and 162 in FIG. 9 and shown in Table 3, to the average stiffness of the center peripheral zones, represented by samples 170 and 172, in FIG. 11 and shown in Table 5

Table 13 shows the ratio of the average stiffness of the central absorbent zones to the average stiffness of the offset zones. The central absorbent zones are represented by samples 130, 132 and 134 in FIG. 9. The offset adjacent zones are represented by samples 142, 144, 146 and 148 in FIG. 9 and shown in Table 4. The offset peripheral zones are represented by samples 174, 176, 178 and 180 in FIG. 11 and shown in Table 6.

Table 14 shows the ratio of the average stiffness of the offset adjacent zones to the average stiffness of the offset peripheral zones in the machine direction. The offset adjacent zones are represented by samples 142, 144, 146 and 148 in FIG. 9 and shown in Table 4. The offset peripheral zones are represented by samples 174, 176, 178 and 180 in FIG. 11 and shown in Table 6.

Table 15 shows the width of dimensions A, B, C and D in various sanitary napkins. For sanitary napkins identified as Invention H and Invention M, the width dimensions A, B, C and D are shown in FIG. 13. For sanitary napkins identified as Invention A, dimensions B and D are equal because there is no hourglass shape for the tissue layers.

Table 16 shows ratios of certain width dimensions for the dimensions provided in Table 15.

Tables 17, 18 and 19 show the caliper or thickness of sanitary napkins of the present invention for the various zones within the sanitary napkin. Tables 20 and 21 show the caliper or thickness of commercially available sanitary napkins at comparable locations to where the various zones of the present invention would be located. Caliper refers to thickness measured by a caliper device. The center adjacent zone desirably has a caliper in the range of from about 0.5 mm. to about 3.0 mm. More desirably, the center adjacent zone has a caliper in the range of about 1.3 mm. to about 1.5 mm.

TABLE 1

STIFFNESS OF THE CENTRAL ABSORBENT ZONE
in Machine Direction

|  | No. of Samples | Gurley Stiffness in milligrams | | |
|---|---|---|---|---|
|  |  | Average | Minimum | Maximum |
| Invention A: K-C Ultra Thin Pad with Foam | 15 | 111 | 522 | 1532 |
| Invention B: K-C Ultra Thin Pad with Foam | 15 | 2526 | 2020 | 3067 |
| Invention H: K-C Ultra Thin Pad with Foam | 15 | 1109 | 866 | 1354 |
| Invention J: K-C Ultra Thin Pad with Foam | 15 | 1020 | 667 | 1498 |
| Invention M: K-C Ultra Thin Pad with Foam | 15 | 1025 | 755 | 1288 |
| Invention W: K-C Ultra Thin Pad with Foam | 15 | 782 | 477 | 1143 |
| K-C Ultra Thin Pad with Pulp | 15 | 695 | 560 | 905 |
| P&G Whisper Excel (with wings) | 15 | 214 | 133 | 278 |

TABLE 2

STIFFNESS OF THE CENTRAL ABSORBENT ZONE
in Transverse Direction

|  | No. of Samples | Gurley Stiffness in milligrams | | |
|---|---|---|---|---|
|  |  | Average | Minimum | Maximum |
| Invention A: K-C Ultra Thin Pad with Foam | 15 | 893 | 699 | 1310 |
| Invention B: K-C Ultra Thin Pad with Foam | 15 | 1647 | 1154 | 2445 |
| Invention H: K-C Ultra Thin Pad with Foam | 15 | 821 | 616 | 1010 |
| Invention J: K-C Ultra Thin Pad With Foam | 15 | 494 | 297 | 738 |
| Invention M: K-C Ultra Thin Pad with Foam | 15 | 806 | 599 | 977 |
| Invention W: K-C Ultra Thin Pad with Foam | 15 | 512 | 342 | 755 |
| K-C Ultra Thin Pad with Pulp | 15 | 392 | 278 | 560 |
| P&G Whisper Excel (with wings) | 15 | 171 | 104 | 453 |

TABLE 3

STIFFNESS OF CENTER ADJACENT ZONES in Machine Direction

| | No. of Samples | Gurley Stiffness in milligrams | | |
|---|---|---|---|---|
| | | Average | Minimum | Maximum |
| Invention A: K-C Ultra Thin Pad with Foam | 10 | 211 | 172 | 245 |
| Invention B: K-C Ultra Thin Pad with Foam | 10 | 245 | 195 | 289 |
| Invention H: K-C Ultra Thin Pad with Foam | 10 | 297 | 239 | 345 |
| Invention J: K-C Ultra Thin Pad with Foam | 10 | 133 | 99 | 175 |
| Invention M: K-C Ultra Thin Pad with Foam | 10 | 131 | 108 | 168 |
| Invention W: K-C Ultra Thin Pad with Foam | 10 | 169 | 122 | 278 |
| K-C Ultra Thin Pad with Pulp | 10 | 119 | 33 | 267 |
| P&G Whisper Excel (with wings) | 10 | 178 | 145 | 217 |

TABLE 4

STIFFNESS OF OFFSET ADJACENT ZONES in Machine Direction

| | No. of Samples | Gurley Stiffness in milligrams | | |
|---|---|---|---|---|
| | | Average | Minimum | Maximum |
| Invention A: K-C Ultra Thin Pad with Foam | 20 | 198 | 133 | 245 |
| Invention B: K-C Ultra Thin Pad with Foam | 20 | 233 | 181 | 322 |
| Invention H: K-C Ultra Thin Pad with Foam | 20 | 317 | 239 | 411 |
| Invention J: K-C Ultra Thin Pad with Foam | 20 | 198 | 114 | 372 |
| Invention M: K-C Ultra Thin Pad with Foam | 20 | 121 | 97 | 175 |
| Invention W: K-C Ultra Thin Pad with Foam | 20 | 150 | 100 | 225 |
| K-C Ultra Thin Pad With Pulp | 20 | 86 | 20 | 200 |
| P&G Whisper Excel (with wings) | 20 | 167 | 136 | 220 |

TABLE 5

STIFFNESS OF THE CENTER PERIPHERAL ZONES in Machine Direction

| | No. of Samples | Gurley Stiffness in milligrams | | |
|---|---|---|---|---|
| | | Average | Minimum | Maximum |
| Invention A: K-C Ultra Thin Pad with Foam | 10 | 77 | 47 | 110 |
| Invention B: K-C Ultra Thin Pad with Foam | 10 | 78 | 44 | 127 |
| Invention M: K-C Ultra Thin Pad with Foam | 10 | 52 | 28 | 82 |
| K-C Ultra Thin Pad with Pulp | 10 | 25 | 13 | 43 |
| P&G Whisper Excel (with wings) | 10 | 7 | 1 | 14 |

TABLE 6

STIFFNESS OF THE OFFSET PERIPHERAL ZONES in Machine Direction

| | No. of Samples | Gurley Stiffness in milligrams | | |
|---|---|---|---|---|
| | | Average | Minimum | Maximum |
| Invention A: K-C Ultra Thin Pad with Foam | 20 | 79 | 54 | 115 |
| Invention B: K-C Ultra Thin Pad with Foam | 20 | 70 | 30 | 109 |
| Invention M: K-C Ultra Thin Pad with Foam | 20 | 72 | 34 | 104 |
| K-C Ultra Thin Pad with Pulp | 20 | 35 | 17 | 76 |
| P&G Whisper Excel (with wings) | 20 | 87 | 20 | 178 |

TABLE 7

DIFFERENCE IN AVERAGE STIFFNESS BETWEEN THE CENTRAL ABSORBENT ZONES AND THE ADJACENT ZONES in Machine Direction

| | Gurley Stiffness in milligrams | |
|---|---|---|
| | Center Adjacent Zones | Center Peripheral Zones |
| Invention A: K-C Ultra Thin Pad with Foam | 900 | 1034 |
| Invention B: K-C Ultra Thin Pad with Foam | 2282 | 2448 |
| Invention H: K-C Ultra Thin Pad with Foam | 812 | N.D. |
| Invention J: K-C Ultra Thin Pad with Foam | 887 | N.D. |
| Invention M: K-C Ultra Thin Pad with Foam | 894 | 973 |
| Invention W: K-C Ultra Thin Pad with Foam | 613 | N.D. |
| K-C Ultra Thin Pad with Pulp | 576 | 670 |
| P&G Whisper Excel (with wings) | 36 | 207 |

TABLE 8

DIFFERENCE IN AVERAGE STIFFNESS BETWEEN THE CENTER ADJACENT ZONES AND THE CENTER PERIPHERAL ZONES in Machine Direction

| | Gurley Stiffness in milligrams |
|---|---|
| Invention A: K-C Ultra Thin Pad with | 134 |
| Invention B: K-C Ultra Thin Pad with Foam | 167 |
| Invention H: K-C Ultra Thin Pad with Foam | N.D. |
| Invention J: K-C Ultra Thin Pad with Foam | N.D. |
| Invention M: K-C Ultra Thin Pad with Foam | 79 |
| Invention W: K-C Ultra Thin Pad with Foam | N.D. |
| K-C Ultra Thin Pad with Pulp | 93 |
| P&G Whisper Excel (with wings) | 171 |

TABLE 9

DIFFERENCE IN AVERAGE STIFFNESS BETWEEN THE CENTRAL ABSORBENT ZONE AND THE OFFSET ZONES in Machine Direction

| | Gurley Stiffness in milligrams | |
|---|---|---|
| | Offset Adjacent Zones | Offset Peripheral Zones |
| Invention A: K-C Ultra Thin Pad with Foam | 913 | 1032 |
| Invention B: K-C Ultra Thin Pad with Foam | 2293 | 2456 |
| Invention H: K-C Ultra Thin Pad with Foam | 792 | N.D. |
| Invention J: K-C Ultra Thin Pad with Foam | 822 | N.D. |
| Invention M: K-C Ultra Thin Pad with Foam | 904 | 953 |
| Invention W: K-C Ultra Thin Pad with Foam | 632 | N.D. |
| K-C Ultra Thin Pad with Pulp | 610 | 660 |
| P&G Whisper Excel (with wings) | 35 | 127 |

TABLE 10

DIFFERENCE IN AVERAGE STIFFNESS BETWEEN THE OFFSET ADJACENT ZONES AND THE OFFSET PERIPHERAL ZONES in Machine Direction

| | Gurley Stiffness in milligrams |
|---|---|
| Invention A: K-C Ultra Thin Pad with Foam | 119 |
| Invention B: K-C Ultra Thin Pad with Foam | 162 |
| Invention H: K-C Ultra Thin Pad with Foam | N.D. |

TABLE 10-continued

DIFFERENCE IN AVERAGE STIFFNESS BETWEEN THE OFFSET ADJACENT ZONES AND THE OFFSET PERIPHERAL ZONES in Machine Direction

| | Gurley Stiffness in milligrams |
|---|---|
| Invention J: K-C Ultra Thin Pad with Foam | N.D. |
| Invention M: K-C Ultra Thin Pad with Foam | 49 |
| Invention W: K-C Ultra Thin Pad with Foam | N.D. |
| K-C Ultra Thin Pad with Pulp | 50 |
| P&G Whisper Excel (with wings) | 80 |

TABLE 11

RATIO OF THE AVERAGE STIFFNESS OF THE CENTRAL ABSORBENT ZONE TO THE AVERAGE STIFFNESS OF THE CENTER ADJACENT ZONES AND TO THE CENTER PERIPHERAL ZONES in Machine Direction

| | Center Adjacent Zones | Center Peripheral Zones |
|---|---|---|
| Invention A: K-C Ultra Thin Pad with Foam | 5.3 | 14.5 |
| Invention B: K-C Ultra Thin Pad with Foam | 10.3 | 32.4 |
| Invention H: K-C Ultra Thin Pad with Foam | 3.7 | N.D. |
| Invention J: K-C Ultra Thin Pad with Foam | 7.7 | N.D. |
| Invention M: K-C Ultra Thin Pad with Foam | 7.8 | 19.8 |
| Invention W: K-C Ultra Thin Pad with Foam | 4.6 | N.D. |
| K-C Ultra Thin Pad with Pulp | 5.9 | 27.4 |
| P&G Whisper Excel (with wings) | 1.1 | 30.1 |

TABLE 12

RATIO OF AVERAGE STIFFNESS OF CENTER ADJACENT ZONES TO AVERAGE STIFFNESS OF CENTER PERIPHERAL ZONES in Machine Direction

| | Averages |
|---|---|
| Invention A: K-C Ultra Thin Pad with Foam | 2.8 |
| Invention B: K-C Ultra Thin Pad with Foam | 3.1 |
| Invention H: K-C Ultra Thin Pad with Foam | N.D. |
| Invention J: K-C Ultra Thin Pad with Foam | N.D. |
| Invention M: K-C Ultra Thin Pad with Foam | 2.5 |
| Invention W: K-C Ultra Thin Pad with Foam | N.D. |
| K-C Ultra Thin Pad with Pulp | 4.7 |
| P&G Whisper Excel (with wings) | 25.0 |

TABLE 13

RATIO OF AVERAGE STIFFNESS OF CENTRAL ABSORBENT ZONES TO AVERAGE STIFFNESS OF THE OFFSET ZONES in Machine Direction

|  | Offset Adjacent Zones | Offset Peripheral Zones |
|---|---|---|
| Invention A: K-C Ultra Thin Pad with Foam | 5.6 | 14.1 |
| Invention B: K-C Ultra Thin Pad with Foam | 10.8 | 36.0 |
| Invention H: K-C Ultra Thin Pad with Foam | 3.5 | N.D. |
| Invention J: K-C Ultra Thin Pad with Foam | 5.2 | N.D. |
| Invention M: K-C Ultra Thin Pad with Foam | 8.5 | 14.2 |
| Invention W: K-C Ultra Thin Pad with Foam | 5.2 | N.D. |
| K-C Ultra Thin Pad with Pulp | 8.1 | 19.7 |
| P&G Whisper Excel (with wings) | 1.3 | 2.5 |

TABLE 14

RATIO OF AVERAGE STIFFNESS OF OFFSET ADJACENT ZONES TO AVERAGE STIFFNESS OF OFFSET PERIPHERAL ZONES in Machine Direction

|  | Ratio of Averages |
|---|---|
| Invention A: K-C Ultra Thin Pad with Foam | 2.5 |
| Invention B: K-C Ultra Thin Pad with Foam | 3.3 |
| Invention H: K-C Ultra Thin Pad with Foam | N.D. |
| Invention J: K-C Ultra Thin Pad with Foam | N.D. |
| Invention M: K-C Ultra Thin Pad with Foam | 1.7 |
| Invention W: K-C Ultra Thin Pad with Foam | N.D. |
| K-C Ultra Thin Pad with Pulp | 2.4 |
| P&G Whisper Excel (with wings) | 1.9 |

TABLE 15

PAD WIDTH MEASUREMENTS

| PRODUCT | (A) CENTRAL ABSORBENT ZONE WIDTH, inches millimeters | (B) ABSORBENT ZONE WIDTH, inches millimeters | (C) PAD WIDTH inches millimeters | (D) RESILIENT LAYER WIDTH inches millimeters |
|---|---|---|---|---|
| Invention A: K-C Ultra Thin Pad with Foam | 1.25 in. 32 mm. | 2.835 in. 72 mm. | 3.62 in. 92 mm. | 2.835 in. 72 mm. |
| Invention H: K-C Ultra Thin Pad with Foam | 1.25 in. 32 mm. | 2.125 in. | 3.75 in. | 3.75 in. |
| Invention M: K-C Ultra Thin Pad with Foam | 1.25 in. 32 mm. | 2.125 in. | 3.75 in. 95 mm. | 3.75 in. |
| K-C Ultra Thin Pad with Pulp | 1.25 in. 32 mm. | 2.125 in. 54 mm. | 3.75 in. 95 mm. | N.D. |
| P&G Whisper Excel with Wings | 2.57 in. 70 mm. | 2.75 in. 70 mm. | 3.5 in. 89 mm. | N.D. |

TABLE 16

PAD WIDTH RATIOS

| PRODUCT | A/B* 100%, percent | A/C* 100% percent | A/D* 100% percent | C/4 in |
|---|---|---|---|---|
| Invention A: K-C Ultra Thin Pad with Foam | 44 | 34 | 44 | 0.90 |
| Invention H: K-C Ultra Thin Pad with Foam | 59 | 33 | 33 | 0.94 |
| Invention M: K-C Ultra Thin Pad with Foam | 59 | 33 | 40 | 0.94 |
| K-C Ultra Thin Pad with Pulp | 59 | 33 | N.D. | 0.94 |
| P&G Whisper Excel with Wings | 100 | 79 | N.D. | 0.88 |

TABLE 17

CALIPER OF INVENTION A: K-C ULTRA THIN PAD WITH FOAM

| Central Absorbent Zone | 3.095 mm |
|---|---|
| Center Adjacent Zones | 1.681 mm |
| Offset Adjacent Zones | 1.699 mm |
| Center Peripheral Zones | 1.130 mm |
| Offset Peripheral Zones | 1.264 mm |
| Peripheral Edges | 0.376 mm |

TABLE 18

CALIPER OF INVENTION B: K-C ULTRA THIN PAD WITH FOAM

| Central Absorbent Zone | 3.11 mm |
|---|---|
| Center Adjacent Zones | 1.537 mm |
| Offset Adjacent Zones | 1.567 mm |
| Center Peripheral Zones | 0.846 mm |
| Offset Peripheral Zones | 1.223 mm |
| Peripheral Edges | 0.343 mm |

TABLE 19

CALIPER OF INVENTION M: K-C ULTRA THIN PAD WITH FOAM

| | |
|---|---|
| Central Absorbent Zone | 3.62 mm |
| Center Adjacent Zones | 1.330 mm |
| Offset Adjacent Zones | 1.650 mm |
| Center Peripheral Zones | 1.105 mm |
| Offset Peripheral Zones | 1.223 mm |
| Peripheral Edges | 0.316 mm |

TABLE 20

CALIPER OF K-C ULTRA THIN PAD WITH PULP

| | |
|---|---|
| Central Absorbent Zone | 2.486 mm |
| Center Adjacent Zones | 0.859 mm |
| Offset Adjacent Zones | 0.705 mm |
| Center Peripheral Zones | 0.292 mm |
| Offset Peripheral Zones | 0.415 mm |
| Peripheral Edges | 0.363 mm |

TABLE 21

CALIPER OF P&G WHISPER EXCEL (with wings)

| | |
|---|---|
| Central Absorbent Zone | 1.546 mm |
| Center Adjacent Zones | 1.516 mm |
| Offset Adjacent Zones | 1.574 mm |
| Center Peripheral Zones | 0.480 mm |
| Offset Peripheral Zones | 1.161 mm |
| Peripheral Edges | 0.444 mm |

Absorbency Testing

The amount of body fluid which can be absorbed by the sanitary napkins 15, 40, 50 and 80 can be determined using a saline solution in the following test. In performing this test, one napkin is sufficient. The sanitary napkin to be tested is first conditioned by leaving it in a room which is at 21±1 degree Centigrade and at 50±2% relative humidity for a period of two hours. If the napkin contains a peel strip, this is removed. The entire napkin, minus any peel strip, is weighed to the nearest 0.1 gram. The napkin is then submerged in a beaker of stabilized isotonic saline which contains no preservatives. A suitable sterile saline is commercially sold by Baxter Healthcare Corp. of Deerfield, Ill. U.S.A. under catalog no. B3158-2. The napkin is totally submerged and is not bent or otherwise twisted or folded. The napkin is submerged for 10 minutes. The napkin is removed from the saline and suspended for two minutes in a vertical position to allow the saline to drain out of the napkin. The napkin is then placed with the bodyside cover face down on an absorbent blotter. The blotter can be filter paper no. ED 631-25 available from the Ahlstrom Filtration Inc., Mount Holly Springs, Pa. 17065 U.S.A. A uniform 17.6 grams per square centimeter load is placed over the napkin to squeeze out excess fluid. The absorbent blotter is replaced every 30 seconds until the amount of fluid transferred to the absorbent blotter is less than 0.5 grams in a 30 second period. Next, the napkin is weighed to the nearest 0.1 gram and the dry weight of the napkin is subtracted. The difference in grams is the capacity of the napkin.

Absorbency Testing was conducted for the entire napkins 15 and 50 and recorded as the "Total Capacity". The absorbency of the central absorbent zones 102 and 122 were also tested and recorded as the "Test Capacity."

For sanitary napkins 50, the Third Embodiment, Invention B, the average Total Capacity of five samples was 38.2 grams. The average Test Capacity of five samples was 22.3 grams.

For sanitary napkins 15, the First Embodiment, Invention W, the average Total Capacity of five samples was 37.9 grams. The average Test Capacity of five samples was 22.5 grams.

For another set of five samples of the sanitary napkin 15, the First Embodiment, the average Total Capacity of five samples was 32.8 grams. The average Test Capacity of five samples was 21.4 grams.

Samples of the K-C Ultra Thin Pad with Pulp, a commercially available sanitary napkin, were also tested. The average Total Capacity of the samples was 33.57 grams. The average Test Capacity of the samples was 19.81 grams.

Samples of a P&G Always Ultra Plus product, a commercially available sanitary napkin were also tested. The average Total Capacity of the samples was 37.02 grams. The average Test Capacity of the samples was 14.08 grams.

Other Embodiments

While the invention has been described in detail with respect to specific embodiments thereof, it will be appreciated that those skilled in the art, upon attaining an understanding of the foregoing description, may readily conceive of alterations to, variations of and equivalents to these embodiments. Accordingly, the scope of the present invention should be assessed as that of the appended claims and any equivalents thereto.

For example, the invention has been described in the context of sanitary napkins. But, the invention is also applicable to other absorbent articles, such as thick sanitary napkins, diapers, panty liners, incontinent products, training pants, bandages, and the like. In other embodiments, a separate baffle may be omitted and the resilient layer may also function as the baffle.

The shape of the absorbent article may vary. It may be less rounded at the ends and more rectangular. More of the layers or all of the layers may be hourglass or racetrack in shape. The resilient layer may be positioned in a different location in reference to the other layers. The shape of the resilient layer may vary in comparison to the other layers. Other materials selected for the resilient layer may have a rebound resilience of about 50% or in the range of from about 25% to about 95%. The resilient layer may be discontinuous. For example, it may have holes in it. The number of layers of tissue may vary or may be eliminated. More or less adhesive may be used within the layers. A different absorbent means may be used, such as one which does not contain superabsorbent or hydrocolloidal material. The primary or significant absorbent means may not be the central stiffening means that resists twisting. The absorbent article, such as a sanitary napkin may have a central stiffening means to resist twisting, and one or more separate absorbent layers or other absorbent means that may not be as stiff as the central stiffening means.

We claim:

1. An absorbent article having a central longitudinal axis, a caliper of less than about 5 millimeters, and a total width adapted to span the width of a user's labia majora, said absorbent article comprising:

a) an absorbent means having a predetermined length and width, a central longitudinal axis substantially aligned along the central longitudinal axis of said absorbent article, said absorbent means having the capacity to absorb at least 10 grams of body fluid; and b) a substantially resilient layer comprising a closed cell, polyethylene foam having a width ranging from 60% to 100% of the total width of said absorbent article, said resilient layer being sufficiently resilient to resist bunching, as indicated by a Circular Bend Flex in the range of from about 9 to about 42 grams at a rebound resiliency of 50%.

2. An absorbent article adapted to receive and absorb body fluid and having a central longitudinal axis, said absorbent article comprising:

a) an absorbent means having a predetermined length and width, a central longitudinal axis substantially aligned along the central longitudinal axis of said absorbent article, said absorbent means capable of absorbing at least 10 grams of the body fluid deposited on said absorbent article; and b) a substantially non-absorbent, substantially resilient layer positioned adjacent to said absorbent means, said resilient layer comprising a closed cell, polyethylene foam having a width greater than the predetermined width of said absorbent means and adapted to prevent bunching, as indicated by a Circular Bend Flex in the range of from about 9 to about 42 grams at a rebound resiliency of 50%, and wherein said absorbent article has a caliper of less than about 5 mm.

3. The absorbent article of claim 2 wherein said absorbent article has a body-facing side and a total width transverse to said longitudinal axis of said absorbent article defined by a distance from an outer side edge to an opposite outer side edge of the body-facing side of the absorbent article and said absorbent means has a width less than about 60% of the total width of said absorbent article.

4. The absorbent article of claim 2 wherein said substantially resilient layer has a length at least equal to the predetermined length of the absorbent means.

5. The absorbent article of claim 2 wherein said absorbent article comprises at least a central absorbent zone and a peripheral zone, wherein said central absorbent zone is thicker in caliper, more absorbent and stiffer than zone; and said peripheral zone.

6. The absorbent article of claim 5 further comprising an adjacent zone located between said central absorbent zone and said peripheral zone, said adjacent zone being less thick in caliper, less absorbent and less stiff than said central absorbent zone; said adjacent zone being thicker in caliper, more absorbent and stiffer than said peripheral zone.

7. The absorbent article of claim 6 wherein said central absorbent zone has a Gurley stiffness in the range of from about 782 milligrams to about 2526 milligrams, said adjacent zone has within it a center adjacent zone, said center adjacent zone has a Gurley stiffness in the range of from about 99 mg. to about 345 mg. and said center adjacent zone has a caliper in the range of from about 0.5 mm. to about 3.0 mm.

8. The absorbent article of claim 2 wherein said foam has a thickness of less than 1/8 inch.

9. The absorbent article of claim 2 wherein said resilient layer has a garment facing side and said absorbent article further comprises a baffle disposed on the garment facing side of said resilient layer.

10. The absorbent article of claim 2 further comprising a liquid-pervious cover sheet.

11. The absorbent article of claim 2 further comprising at least one tissue layer that extends beyond the absorbent means.

12. The absorbent article of claim 11 wherein said absorbent means has a garment-facing side and said at least one tissue layer is disposed on said garment-facing side of said absorbent means.

13. The absorbent article of claim 11 wherein said absorbent means has a body-facing side and said at least one tissue layer is disposed on said body-facing side of said absorbent means.

14. The absorbent article of claim 11 wherein said absorbent means has a body-facing side and a garment-facing side and said at least one tissue layer includes two tissue layers, said two tissue layer disposed on both said garment-facing side and said body-facing side of said absorbent means, respectively.

15. The absorbent article of claim 1 wherein said absorbent means has a body-facing side and said absorbent article further comprises a transfer layer disposed on said body-facing side of said absorbent means.

16. A sanitary napkin having a garment-facing side, a caliper of less than about 5 millimeters, and a central longitudinal axis, said sanitary napkin comprising:

a) a liquid-impermeable baffle disposed on said garment-facing side of said sanitary napkin, said baffle having a body-facing side;

b) a substantially non-absorbent, resilient layer comprising a closed cell, polyethylene foam and being disposed on said body-facing side of said baffle, said resilient layer adapted to prevent bunching, as indicated by a Circular Bend Flex in the range of from about 9 to about 42 grams at a rebound resiliency of 50%, said resilient layer having a body-facing side; and c) an absorbent means disposed adjacent to said body-facing side of said resilient layer, said absorbent means having a central longitudinal axis substantially aligned along the central longitudinal axis of said napkin, said absorbent means adapted to resist twisting and capable of absorbing at least 10 grams of body fluid deposited on said napkin.

17. The sanitary napkin of claim 16 wherein said napkin comprises at least a central absorbent zone and a peripheral zone, wherein said central absorbent zone is thicker in caliper, more absorbent and stiffer than the peripheral zone and wherein said peripheral zone is located at an outer side edge of the napkin.

18. The sanitary napkin of claim 17 further comprising an adjacent zone located between said central absorbent zone and said peripheral zone, said adjacent zone being less thick in caliper, less absorbent and less stiff than said central absorbent zone; said adjacent zone being thicker in caliper, more absorbent and stiffer than said peripheral zone.

19. The sanitary napkin of claim 17 wherein said central absorbent zone has a Gurley stiffness in the range of from about 782 milligrams to about 2526 milligrams.

20. A sanitary napkin having a central longitudinal axis, a body-facing side and a total width transverse to said longitudinal axis defined by a distance from an outer side edge of the body-facing side of the sanitary napkin to an opposite outer side edge of the body-facing side, said sanitary napkin comprising:

a. a liquid pervious cover sheet;

b. an absorbent means having a central longitudinal axis substantially aligned along the central longitudinal axis of said napkin, said absorbent means capable of absorbing at least 10 grams of body fluid deposited on said napkin and being sufficiently stiff to resist twisting of the sanitary napkin during use; and c. a substantially resilient layer comprising a closed celled polyethylene foam having a width ranging from 60% to 100% of the total width of said body-facing side of the sanitary napkin and being sufficiently resilient to resist bunching as indicated by a Circular Bend Flex in the range of from 9 to about 42 grams at a rebound resiliency of about 50% and wherein said sanitary napkin has a caliper of less than about 5 mm.

21. The sanitary napkin of claim 20 wherein said absorbent means has a width less than 60% of the total width of said sanitary napkin.

22. The sanitary napkin of claim 21 wherein said napkin comprises at least a central absorbent zone and a peripheral zone, wherein said central zone is thicker in caliper and stiffer than said peripheral zone and wherein said peripheral zone is located at an outer side edge of the napkin.

23. The sanitary napkin of claim 22 further comprising an adjacent zone located between said central absorbent zone and said peripheral zone, said adjacent zone being less thick in caliper and less stiff than said central absorbent zone.

24. The sanitary napkin of claim 23 wherein said central absorbent zone has a Gurley stiffness in the range of from about 782 milligrams to about 2526 milligrams, said adjacent zone has within it a center adjacent zone, said center adjacent zone has a Gurley stiffness in the range of from about 99 mg. to about 345 mg., said center adjacent zone has a caliper in the range of from about 0.5 mm. to about 3.0 mm., and the ratio of the average stiffness of the central absorbent zone to the average stiffness of the central adjacent zone is in the range of from about 3.7:1 to about 10.3:1.

* * * * *